(12) United States Patent
Tamarkin et al.

(10) Patent No.: US 8,709,385 B2
(45) Date of Patent: Apr. 29, 2014

(54) POLOXAMER FOAMABLE PHARMACEUTICAL COMPOSITIONS WITH ACTIVE AGENTS AND/OR THERAPEUTIC CELLS AND USES

(75) Inventors: Dov Tamarkin, Maccabim (IL); Alex Besonov, Rehovot (IL); Tal Berman, Rishon Lezion (IL); David Schuz, Moshav Gimzu (IL); Elana Gazal, Rehovot (IL)

(73) Assignee: Foamix Ltd., Rehovot (IL)

( * ) Notice: Subject to any disclaimer, the term of this patent is extended or adjusted under 35 U.S.C. 154(b) by 161 days.

(21) Appl. No.: 12/836,444

(22) Filed: Jul. 14, 2010

(65) Prior Publication Data

US 2011/0008266 A1  Jan. 13, 2011

Related U.S. Application Data

(63) Continuation of application No. PCT/IB2009/005012, filed on Jan. 14, 2009.

(60) Provisional application No. 61/020,950, filed on Jan. 14, 2008, provisional application No. 61/077,779, filed on Jul. 2, 2008.

(51) Int. Cl.
| | |
|---|---|
| A61K 8/00 | (2006.01) |
| A61K 8/02 | (2006.01) |
| A61K 9/00 | (2006.01) |
| A61K 9/12 | (2006.01) |
| A61K 31/00 | (2006.01) |
| A61K 31/60 | (2006.01) |
| A61P 17/00 | (2006.01) |
| A61P 31/00 | (2006.01) |
| A61P 29/00 | (2006.01) |

(52) U.S. Cl.
USPC ......... 424/43; 424/45; 424/78.05; 424/78.07; 514/859; 514/861; 514/871; 514/944; 514/945

(58) Field of Classification Search
CPC ........... A61K 31/00; A61K 8/00; A61K 9/00; A61K 9/12; A61K 31/60; A61P 29/00; A61P 31/00
USPC ........ 424/43, 45, 78.05, 78.07; 514/859, 861, 514/871, 944, 945
See application file for complete search history.

(56) References Cited

U.S. PATENT DOCUMENTS

| | | | |
|---|---|---|---|
| 1,159,250 A | 11/1915 | Moulton | |
| 1,666,684 A | 4/1928 | Carstens | |
| 1,924,972 A | 8/1933 | Beckert | |
| 2,085,733 A | 7/1937 | Bird | |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,767,712 A | 10/1956 | Waterman | |
| 2,968,628 A | 1/1961 | Reed | |
| 3,004,894 A | 10/1961 | Johnson et al. | |
| 3,062,715 A | 11/1962 | Reese et al. | |
| 3,067,784 A | 12/1962 | Gorman | |
| 3,092,255 A | 6/1963 | Hohman | |
| 3,092,555 A | 6/1963 | Horn | |
| 3,141,821 A | 7/1964 | Compeau | |
| 3,142,420 A | 7/1964 | Gawthrop | |
| 3,144,386 A | 8/1964 | Brightenback | |
| 3,149,543 A | 9/1964 | Naab | |
| 3,154,075 A | 10/1964 | Weckesser | |
| 3,178,352 A | 4/1965 | Erickson | |
| 3,236,457 A | 2/1966 | Kennedy et al. | |
| 3,244,589 A | 4/1966 | Sunnen | |
| 3,252,859 A | 5/1966 | Silver | |
| 3,261,695 A | 7/1966 | Sienkiewicz | |
| 3,263,867 A | 8/1966 | Lehmann | |
| 3,263,869 A | 8/1966 | Corsette | |
| 3,298,919 A | 1/1967 | Bishop et al. | |
| 3,301,444 A | 1/1967 | Wittke | |
| 3,303,970 A | 2/1967 | Breslau et al. | |
| 3,330,730 A | 7/1967 | Hernandez | |
| 3,333,333 A | 8/1967 | Noack | |
| 3,346,451 A | 10/1967 | Collins et al. | |
| 3,366,494 A | 1/1968 | Bower et al. | |

(Continued)

FOREIGN PATENT DOCUMENTS

| | | |
|---|---|---|
| AU | 198780257 | 9/1986 |
| CA | 2422244 | 9/2003 |

(Continued)

OTHER PUBLICATIONS

Partial International Search Report issued for PCT/IB2009/005012 (3 pages).
U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.

(Continued)

*Primary Examiner* — Mina Haghighatian
(74) *Attorney, Agent, or Firm* — Fish & Richardson P.C.

(57) ABSTRACT

Pharmaceutical or cosmetic compositions and methods for their use are provided comprising water and a surfactant polymer system comprising a Poloxamer at a concentration of about 0.1% to about 15% by weight; wherein when the Poloxamer is between about 0.1% to about 5% Poloxamer. The composition can further comprise a supporting agent comprising a non-ionic surface active agent or a supporting agent comprising a non surfactant polymer or polysaccharide and an active agent, where the Poloxamer is capable of fixing the composition on delivery to a body surface. There are further provided therapeutic cell compositions and their uses.

31 Claims, 3 Drawing Sheets

(56) References Cited

U.S. PATENT DOCUMENTS

| | | |
|---|---|---|
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |

(56) References Cited

U.S. PATENT DOCUMENTS

| | | |
|---|---|---|
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |

(56) References Cited

U.S. PATENT DOCUMENTS

| | | |
|---|---|---|
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,358,541 B1 | 3/2002 | Goodman |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,455,076 B1 | 9/2002 | Hahn et al. |
| 6,468,989 B1 | 10/2002 | Chang et al. |
| 6,479,058 B1 | 11/2002 | McCadden |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |

(56) References Cited

U.S. PATENT DOCUMENTS

| | | |
|---|---|---|
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 * | 8/2009 | Tamarkin et al. ............... 424/43 |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,793,807 B2 | 9/2010 | Goujon et al. |
| 7,820,145 B2 * | 10/2010 | Tamarkin et al. ............... 424/45 |
| 7,960,416 B2 | 6/2011 | Sato et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 * | 2/2005 | Tamarkin et al. ............... 424/45 |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |

(56) References Cited

U.S. PATENT DOCUMENTS

| | | |
|---|---|---|
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0221194 A1 | 9/2010 | Loupenok |
| 2011/0002857 A1 | 1/2011 | Tamarkin et al. |
| 2011/0002969 A1 | 1/2011 | Serraima et al. |
| 2011/0212033 A1 | 9/2011 | Tamarkin et al. |
| 2011/0268665 A1 | 11/2011 | Tamarkin et al. |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0 156 507 | 10/1985 |
| EP | 0 186 453 | 7/1986 |
| EP | 0 211 550 | 2/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |

(56) References Cited

FOREIGN PATENT DOCUMENTS

| | | |
|---|---|---|
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 734 927 | 12/2006 |
| EP | 1 758 547 | 3/2007 |
| EP | 1 584 324 | 11/2007 |
| EP | 1 889 609 | 2/2008 |
| FR | 2 591 331 | 6/1987 |
| FR | 2 640 942 | 6/1990 |
| FR | 2 736 824 | 1/1997 |
| FR | 2 774 595 | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |
| FR | 2 860 976 | 4/2005 |
| FR | 2 915 891 | 11/2008 |
| GB | 808 104 | 1/1959 |
| GB | 808 105 | 1/1959 |
| GB | 922 930 | 4/1963 |
| GB | 933 486 | 8/1963 |
| GB | 998 490 | 7/1965 |
| GB | 1 026 831 | 4/1966 |
| GB | 1 033 299 | 6/1966 |
| GB | 1 081 949 | 9/1967 |
| GB | 1 121 358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |
| GB | 1 353 381 | 5/1974 |
| GB | 1 376 649 | 12/1974 |
| GB | 1 397 285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2 114 580 | 8/1983 |
| GB | 2 153 686 | 8/1985 |
| GB | 2 172 298 | 9/1986 |
| GB | 2 206 099 | 12/1988 |
| GB | 2 166 651 | 5/1996 |
| GB | 2 337 461 | 11/1999 |
| GB | 2 367 809 | 4/2002 |
| GB | 2 406 330 | 3/2005 |
| GB | 2 406 791 | 4/2005 |
| IL | 49491 | 9/1979 |
| IL | 152 486 | 5/2003 |
| JP | S48-92282 | 11/1973 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 1100111 | 4/1989 |
| JP | 1156906 | 6/1989 |
| JP | 2184614 | 7/1990 |
| JP | 2255890 | 10/1990 |
| JP | 4282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 2008/040899 | 2/1996 |
| JP | 8501529 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000/080017 | 3/2000 |
| JP | 2000/128734 | 5/2000 |
| JP | 2000/191429 | 7/2000 |
| JP | 2000/239140 | 9/2000 |
| JP | 2000/351726 | 12/2000 |
| JP | 2000/354623 | 12/2000 |
| JP | 2001/002526 | 1/2001 |
| JP | 2001/019606 | 1/2001 |
| JP | 2001/072963 | 3/2001 |
| JP | 2002/012513 | 1/2002 |
| JP | 2002/047136 | 2/2002 |
| JP | 2002/524490 | 8/2002 |
| JP | 2002/302419 | 10/2002 |
| JP | 2003/012511 | 1/2003 |
| JP | 2003/055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005/350378 | 12/2005 |
| JP | 2006/008574 | 1/2006 |
| JP | 2006/036317 | 2/2006 |
| JP | 2006/103799 | 4/2006 |
| JP | 2006525145 | 11/2006 |
| JP | 2007/131539 | 5/2007 |
| KR | 143232 | 7/1998 |
| KR | 2001/003063 | 1/2001 |
| RU | 2277501 | 6/2006 |
| UA | 66796 | 6/2004 |
| WO | 82/01821 | 6/1982 |
| WO | 86/05389 | 9/1986 |
| WO | 88/01502 | 3/1988 |
| WO | 88/01863 | 3/1988 |
| WO | 88/08316 | 11/1988 |
| WO | 89/06537 | 7/1989 |
| WO | 90/05774 | 5/1990 |
| WO | 91/11991 | 8/1991 |
| WO | 92/00077 | 1/1992 |
| WO | 92/05142 | 4/1992 |
| WO | 92/05763 | 4/1992 |
| WO | 92/11839 | 7/1992 |
| WO | 93/25189 | 12/1993 |
| WO | 94/06440 | 3/1994 |
| WO | 96/03115 | 2/1996 |
| WO | 96/19921 | 7/1996 |
| WO | 96/24325 | 8/1996 |
| WO | 96/26711 | 9/1996 |
| WO | 96/27376 | 9/1996 |
| WO | 96/39119 | 12/1996 |

(56) References Cited

FOREIGN PATENT DOCUMENTS

| | | |
|---|---|---|
| WO | 97/03638 | 2/1997 |
| WO | 97/39745 | 10/1997 |
| WO | 98/17282 | 4/1998 |
| WO | 98/18472 | 5/1998 |
| WO | 98/19654 | 5/1998 |
| WO | 98/21955 | 5/1998 |
| WO | 98/23291 | 6/1998 |
| WO | 98/36733 | 8/1998 |
| WO | 98/52536 | 11/1998 |
| WO | 99/08649 | 2/1999 |
| WO | 99/20250 | 4/1999 |
| WO | 99/37282 | 7/1999 |
| WO | 99/53923 | 10/1999 |
| WO | 00/09082 | 2/2000 |
| WO | 00/15193 | 3/2000 |
| WO | 00/23051 | 4/2000 |
| WO | 00/33825 | 6/2000 |
| WO | 00/38731 | 7/2000 |
| WO | 00/61076 | 10/2000 |
| WO | 00/76461 | 12/2000 |
| WO | 01/05366 | 1/2001 |
| WO | 01/08681 | 2/2001 |
| WO | 01/10961 | 2/2001 |
| WO | 01/53198 | 7/2001 |
| WO | 01/54212 | 7/2001 |
| WO | 01/54679 | 8/2001 |
| WO | 01/62209 | 8/2001 |
| WO | 01/70242 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | 02/15860 | 2/2002 |
| WO | 02/15873 | 2/2002 |
| WO | 02/28435 | 4/2002 |
| WO | 02/41847 | 5/2002 |
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/081327 | 8/2006 |
| WO | 2006/091229 | 8/2006 |
| WO | WO-2006/079632 A1 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/085899 | 8/2007 |
| WO | 2007/085902 | 8/2007 |
| WO | 2007/099396 | 9/2007 |
| WO | WO-2007/111962 A2 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | WO 2009090558 | 7/2009 |
| WO | 2009/098595 | 8/2009 |
| WO | 2011/039637 | 4/2011 |
| WO | 2011/039638 | 4/2011 |

OTHER PUBLICATIONS

U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Oct. 21, 2011 at en.wikipedia.org/wiki/Minocycline, 7 pages.
"Reaction Rate" Accessed at en.wikipedia.org/wiki/Reaction_rate on Dec. 18, 2011, 6 pages.
'Niram Chemicals' [online] Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," *Antimicrobial Agents and Chemotherapy*, vol. 35, No. 9, pp. 1799-1803, 1991.
Anton, N. et al. "Water-in-Oil Nano-Emulsion Formation by the phase inversion Temperature Method: A Novel and General Concept, a New Template for Nanoencapsulation," *Proceedings of the 33rd*

(56) References Cited

OTHER PUBLICATIONS

*Annual Meeting and Exposition of the Controlled Release Society*, Jul. 2006, Vienna, Austria, 2 pages.

Arct et al., "Common Cosmetic Hydrophilic Ingredients as Penetration Modifiers of Flavonoids", International Journal of Cosmetic Science, 24(6):357-366 (2002)—Abstract, 1 page.

Arisan, http://www.arisankimya.com/kozmetik.htm Accessed Dec. 10, 2008, 8 pages.

Augsburger, Larry L. et al. "Bubble Size Analysis of High Consistency Aerosol Foams and Its Relationship to Foam Rheology. Effects of Container Emptying, Propellant Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Barry and Badal, "Stability of minocycline, doxycycline, and tetracycline stored in agar plates and microdilution trays," *Current Microbiology*, 1978, 1:33-36.

Barry, B.W. et al, Comparative bio-availability and activity of proprietary topical corticosteroid preparations: vasoconstrictor assays on thirty-one ointments, British Journal of Dermatology, 93, 563-571, 1975.

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926- 622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

D.W.A. Sharp Dictionary of Chemistry, Penguin Books, 1983, 3 pages.

Dalby, "Determination of Drug Solubility in Aerosol Propellants," Pharmaceutical Research, vol. 8, No. 9, 1991, pp. 1206-1209.

Dawber, et al., "Hypertrichosis in Females Applying Minoxidil Topical Solution and in Normal Controls", JEADV, 17:271-275 (2003).

Denatonium Benzoate http://www.newdruginfo.com/pharmaceopeia/usp28/v28230/usp28nf23s0.sub.--m- 22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

Disorder. (2007). In the American Heritage Dictionary of the English Language. Retrieved from http://www.credoreference.com/entry/hmdictenglang/disorder. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006; 111(2): 145-51.

Edwards, "Imiquimod in Clinical Practice", J. Am Acad Dermatol., 43(1, Pt 2):S12-S17 (2000)—Abstract, 1 page.

Emulsifiers with HLB values. http://www.theherbarie.com/files/resources-center/formulating/Emulsifiers- .sub.--HLB.sub.--Values.pdf accessed Aug. 5, 2009 (3 pps).

Encyclopedia of Pharmaceutical Technology, Second Edition, vol. 3, Copyright 2002, 4 pages.

Esposito, E. et al. "Nanosystems for Skin Hydration: A Comparative Study." International Journal of Cosmetic Science. 29. 2007. pp. 39-47.

Ethanol, Accessed http://www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

(56) References Cited

OTHER PUBLICATIONS

Gelbard et al. "Primary Pediatric Hyperhidrosis: A Review of Current Treatment Options." Pediatric Dermatology. 2008. 25 (6). pp. 591-598.
Gill, A.M, et al., "Adverse Drug Reactions in a Paediatric Intensive Care Unit," Acta Paediatr 84:438-441, 1995.
Gladkikh, "Ascorbic Acid and Methods of Increasing its Stability in Drugs", Translated from Khimiko-Farmatsevticheskii Zhurnal, 4(12):37-42 (1970)—1 page.
Glaser, et al., Hyperhidrosis: A Comprehensive and Practical Approach to Patient Management, Expert Rev. Dermatol. 1(6), 773-775 (2006).
Graves, S. et al. "Structure of Concentrated Nanoemulsions." The Journal of Chemical Physics.. 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irradiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Hormones. Http://www.greenwillowtree.com/Page.bok?file=libido.html. Jan. 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
Hydroxyethylcellulose. Http: //terpconnect.umd.edu/-choi/MSDS/Sigma-Aldrich/HYDROXYETHYL%20CELLULOSE, 5 pages, Jan. 14, 2004.

ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theall7c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006).
Kim, "Stability of Minoxidil in Aqueous Solution", Yakhak Hoechi, 30(5):228-231 (1986)—Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5): 269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Licking Vaginal Dryness without a Prescription. Accessed http://www.estronaut.com/a/vag.sub.--dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.

(56) References Cited

OTHER PUBLICATIONS

Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Martindale. 33 ed. London, Bath Press, 2002. pp. 1073 and 1473.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Index, An Encyclopedia of Chemicals, Drugs, and Biologicals. 13$^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," J. Phys. Chem., 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," J. Electrochemical Soc., 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.

Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural and synthetic triphylite," J. of Power Sources, 2001, 97-98:503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-24 (abstract).
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, Langmuir, 2006, 22: 8337-8345.
Sigma Aldrich, "HLB—Numbers in Lithography Nanopatterning," http://www.sigmaaldrich.com/materials-science/micro-and-nanoelectronics/1- ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http://web.archive.org/web/20030810230608/http://www.skinbio.com/cpserum.- html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 3pages.

(56) References Cited

OTHER PUBLICATIONS

Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatol.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: the Complete Drug Reference. 33rd Edition. London. Pharmaceutical Press. Jun. 21, 2002. pp. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb. 4, 2009, 4 pages.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
Yamada and Chung, "Crystal Chemistry of the Olivine-Type Li($Mn_yFe_{1-y}$)$PO_4$ and ($Mn_yFe_{1-y}$)$PO_4$ as Possible 4 V Cathode Materials for Lithium Batteries," *J. Electrochemical Soc.*, 2001, 148(8): A960-967.
"Coal tars and coal-tar pitches," *Report on Carcinogens*, Twelfth Edition, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.
Fluhr et al., "Glycerol accelerates recovery of barrier function in vivo," *Acta Derm. Venereol,.* 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris,*" *J. Chem. Ecol.*, 11: 1297-1306, 1985.
Knight et al., "Topical diltiazem ointment in the treatment of chronic anal fissure," *Br. J. Surg.*, 2001, 88(4):553-6.
Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196.

(56) References Cited

OTHER PUBLICATIONS

Osborne and Henke, "Skin Penetration Enhancers Cited in the Technical Literature," *Pharm. Technology*, Nov. 1997, pp. 58-86.
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3,4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. Am. Acad. Dermatol.*,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3): 190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/EEC OJ 196, 16.8, 1967, p. 1.
Tzen et al., Lipids, proteins and structure of seed oil bodies from diverse species; *Plant Physiol.*, 1993, 101:267-276.
Brown et al. "Structural dependence of flavonoid interactions with $Cu^{2+}$ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its protoprotection of skin," *J Invest Dermatol*, 2005, 125:826-32.

* cited by examiner

POLOXAMER FOAMABLE PHARMACEUTICAL COMPOSITIONS WITH ACTIVE AGENTS AND/OR THERAPEUTIC CELLS AND USES

CROSS-REFERENCE TO RELATED APPLICATIONS

This application is a continuation of and claims the benefit of priority under 35 U.S.C. §120 to PCT Patent Application No. PCT/IB2009/005012, filed Jan. 14, 2009, entitled "POLOXAMER FOAMABLE PHARMACEUTICAL COMPOSITIONS WITH ACTIVE AGENTS AND/OR THERAPEUTIC CELLS AND USES," which claims the benefit of priority under 35 U.S.C. §119(e) to (1) U.S. Provisional Patent Application No. 61/020,950, filed Jan. 14, 2008, entitled "METHODS FOR POLYMER COMPOSITIONS AND USES THEREOF," and (2) U.S. Provisional Patent Application No. 61/077,779, filed Jul. 2, 2008, entitled "POLOXAMER FOAMABLE PHARMACEUTICAL COMPOSITIONS WITH ACTIVE AGENTS AND OR THERAPEUTIC CELLS AND USES," the contents of all of which are incorporated by reference.

BACKGROUND

External topical administration is an important route for the administration of drugs in disease treatment. Many groups of drugs, including, for example, antibiotic, anti-fungal, anti-inflammatory, anesthetic, analgesic, anti-allergic, corticosteroid, retinoid and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds.

A gel is a semi-rigid, jelly-like colloidal dispersion of a solid with a liquid. The main constituent of gels is liquid, e.g., water, yet they behave like solids due to the addition of a gelling agent. A hydrogel is a network of polymer chains that are water-insoluble, sometimes found as a colloidal gel in which water is the dispersion medium.

Foams are considered a more convenient vehicle for topical delivery of active agents. There are several types of topical foams, including aqueous foams, such as commonly available shaving foams; hydroalcoholic foams, emulsion-based foams, comprising oil and water components, and oleaginous foams, which consist of high oil content. Certain foams, such as shaving foams and hair mousses are not suitable as vehicles for topical drugs, because, for example, they do not absorb into the skin following application (e.g., shaving foams) or because they contain foaming surfactants that can be irritating, (e.g., ionic surfactants, in the case of shaving foam and hair mousse). "Quick-break" thermolabile foams are not ideal because they typically contain substantial amounts of alcohol, which can cause skin drying and irritation and are not convenient as they collapse quickly so that it is difficult to apply them on the target area. Also alcohol containing foams are not suitable for the treatment of open wounds and burns, neither are they suitable for treatment of body cavities, such as the vagina. On the other hand breakable foams, which remain stable on exposure to body temperature but break upon mechanical stimulation allowing easy and convenient spreading are desirable for pharmaceutical use.

Poloxamers, also known by the trade name Pluronics, are nonionic triblock copolymers composed of a central hydrophobic chain of polyoxypropylene (poly(propylene oxide)) flanked by two hydrophilic chains of polyoxyethylene (poly(ethylene oxide)). Because the lengths of the polymer blocks can be customized, many different Poloxamers exist.

Compositions comprising Poloxamers are known in which Poloxamer is merely one ingredient in a complex combination of excipients with or without active pharmaceutical ingredients. Poloxamer has also been used as a constituent of foam produced by mechanical lathering without propellant.

However, most prior art foam compositions that contain Poloxamer lack stability and collapse upon contact with a delivery site in/on a subject. Some pharmaceutical compositions for rectal or vaginal administration have been developed, which comprise: (i) two or more physiologically acceptable substances each in separate parts of the composition which are such that on admixture they react to produce a physiologically acceptable gas; (ii) in at least one part of the composition a polymer stabilizer which is adapted to facilitate the formation of a water-soluble collapsible foam structure; and (iii) in at least one part of the composition a pharmaceutically active substance. These compositions must be delivered using multi-compartment syringes and rely on there being a chemical reaction between parts i) and ii). In the example xanthan and Poloxamer are in combination, wherein the concentration of poloxamer is less than 0.2% and xanthan gum is present in a five fold higher concentration than Poloxamer.

Foam compositions for rectal administration of a solid powder in which the surfactant is Poloxamer have been published. Such compositions include (a) over 25 wt % of a powdered active principle, and (b) 1-20 wt % of a surfactant, and the balance (c) being water. The powdered active principle has a particle size of less than 20 μm.

Also published are compositions of matter without fatty alcohol where the surfactant may be Poloxamer but in the Poloxamer examples the concentration of Poloxamer is 1.6% and a high level of ethyl alcohol (60%) is used to form a foamable delivery system.

A composition has been disclosed comprising (a) monohydric alcohol (b) surfactant comprising a dimethicone surfactant and (c) a builder to improve or provide stability of a foam derived from the composition, in which the builder can be a Poloxamer and wherein the alcohol is 35% to 99.5%. In the examples the Poloxamer foam builder was 0.08% and 0.3% and the alcohol was 65% ethanol 200% proof.

Sprayable germicidal foam compositions to cover wounded skin containing Poloxamer which remain stable for at least an hour and have a half life of 5-7 hours are known. Fatty acids and fatty alcohols are required and the Poloxamer must not exceed 3x the fatty acids or be less than half their combined amount. In the examples Poloxamer was 1.5% to less than 2%.

Foamable suspension gel formulations containing benzyl peroxide in combination with clindamycin have been published in which the gel base contains 0.1 to 2% of a thickening agent. In the Examples, the thickening agent is 1% xantham gum, and it is used with a dispensing or wetting agent (1% Poloxamer 188 and other components), with water being the main component. Although other agents are listed as dispersing or wetting agents only Poloxamer 188 is used in the examples. Good wetting agents are typically considered to be poor foaming agents and vice versa.

Liquid bioadhesive microemulsions or liopsomic dispersions containing proteinic substances are described in which the composition contains a fixing copolymer. At body temperature the viscosity of the compositions is increased and provides an increased residence time at the administration site.

A composition for a foam and a process for preparing have been disclosed in the art, the composition including by weight (a) more than 25% of an active ingredient in powder form; (b) from 1% to 20% of a surfactant; the balance being composed of water, wherein the powder of the active ingredient has a particle size below 20 µm. The surfactant can be a mixture of two surfactants one being a hydrophilic surfactant with a HLB greater than 10 and the other being a polyoxyalkylene-based surfactant (possibly, Poloxamer). In the examples, the amount of hydrophilic surfactant is much greater than the Poloxamer.

The use of Poloxamers with ability to change the sol-gel transition temperature by pH adjustment and by ionic strength adjustment has been disclosed. The preferred polymers are those which form gels at a concentration range of 10% to 50% of the polymer to water.

The use of thermosetting copolymers (Pluronic 127 or Lutrol127) with liposomic dispersions to administer a peptide or protein drug to a body surface is known. In the examples 13%-19.5% copolymers were used.

Other prior art complex compositions include formulations comprising a polymeric agent, which may be a phase change polymer, which alters the composition behavior from fluid-like prior to administration to solid-like upon contact with the target mucosal surface. Such phase change results from external stimuli, such as changes in temperature or pH and exposure to specific ions (e.g., $Ca^{2+}$). Non-limiting examples of phase change polymers include poly(N-isopropylamide), and Poloxamer 407®. High concentrations of Poloxamer are used for gelling.

There are disclosed new, improved, convenient to use, stable foam Poloxamer carrier formulations and pharmaceutical compositions, which are an advance over the prior art.

Foams are complex dispersion systems which do not form under all circumstances. Slight shifts in foam composition, such as by the addition of active ingredients, may destabilize the foam. Foams are very complex and sensitive systems and are not formed at will. Mere addition of basic ingredients like oil, surfactant and propellant is far from sufficient to produce foams of quality that are homogenous, stable, breakable upon mechanical force and can be used to provide a shelf stable pharmaceutical or cosmetic composition. Small deviations may lead to foam collapse. Much consideration needs to be given to facilitate the introduction of an active agent, such as examining compatibility and non reactivity with the various excipients and container and determining shelf life chemical and physical stability.

Neubourg (US 2006/0099151), for example, notes that the stability of foam is strongly dependent on the specific composition of the foam forming components, so that even small deviations in the composition may lead to a collapse of the foam. Gordon et al. (U.S. Pat. No. 3,456,052). also teaches that one cannot generate a good quality foam by simply adding a propellant to a mixture of components:

The term "foam" is a general term that encompasses a range of substances. Accordingly, the context in which "foam" is discussed must be examined carefully. The type and quality of the foam is of critical importance. There are many different types of foams and within each foam type there are many levels of qualities. For example, the froth on the head of beer, lather of shampoo, and lather of shaving cream have been loosely described as foam but all are different from one another. At one end of the cosmetic or pharmaceutical foam spectrum the foam can be long lasting and essentially not readily breakable like shaving foams. At the other end of the spectrum the foam can be quick breaking and collapses upon release.

Thermolabile foams are an example of type of quick breaking foam. They can contain significant amounts of thermolabile substances that aid their collapse upon being exposed to an increased temperature for example when applied to a body surface at 37 C. Upon being exposed to the higher temperature they collapse rapidly. Examples are foam formulations that comprise significant amounts of volatile solvents.

Breakable foam is a specialized type of foam. It is a low density foam that is stable on release at least in the short time span of several minutes, which facilitates application to a target area; but can break readily upon the application of shear force such as gentle rubbing to spread easily over a target surface. It is not thermolabile (and does not melt at skin temperature) and nor does it display late or long delayed expansion over minutes.

Some foams expand slowly whilst others do so quickly. Some foams foam immediately and some demonstrate delayed foaming. Some require mechanical lathering and some expulsion by propellant. Whilst they all fall under the so called term "foam" and may appear to have some common ingredients the results and properties of these products are different.

A suitable foamable formulation for a particular application may present challenges at several levels. For example, a foam formulation may require a stable pre foam formulation; a stable pre foam propellant formulation and ultimately delivery an effective measured amount of active agent to a target. Each of these objectives poses its own unique challenges.

The pharmaceutical and cosmetic foams discussed herein are generated in general terms by manufacturing a suitable foamable carrier composition and loading the carrier in a pressurized valved canister with an appropriate propellant. Upon expelling the canister contents a foam can be released. The type, nature and quality of the foam depends inter alia on the carrier composition, the active agent, the propellant and the method of manufacture and storage. Making a stable (physically and chemically) formulation that can be stored in a canister with a propellant that remains stable and can produce a breakable foam of quality on release is far from trivial.

An additional difficulty frequently encountered with propellant foams is their inability to dispense a satisfactorily uniform application of the medically active ingredient throughout the use of the aerosol container. This is particularly due to the fact that the active material is not stably dispersed in the foamable composition so that it will have a tendency to settle to the bottom. Further, the dispersed material will sometimes clog the spray dispensing valve to further interfere with the uniform dispensing of the medicament. Issues such as the effect of the propellant on the properties of the formulation such as viscosity and miscibility can be critical; whilst the pressure of the propellant; and the shakability of the pre foam formulation with propellant can also effect the ability to achieve satisfactory uniform application as well as the ability to avoid jets and tailing.

SUMMARY

In an aspect there is provided a pharmaceutical or cosmetic composition comprising a foamable carrier comprising:
  a. water;
  b. a surfactant/polymer system comprising a Poloxamer at a concentration of about 0.1% to about 15% by weight:
     i. wherein when the concentration of Poloxamer is between about 0.1% to about 5% Poloxamer the composition further comprises a supporting agent comprising a non-ionic surface active agent; or
     ii. wherein when the concentration of Poloxamer is between about 0.1% to about 5% Poloxamer and the composition further comprises a supporting agent comprising a polymer, or a polysaccharide or a mixture thereof the Poloxamer is capable of fixing the composition on delivery to a body surface; and
  c. an active agent wherein the composition is capable of forming a foam if packaged in a packaging assembly comprising an aerosol container, equipped with a valve and an actuator, capable of releasing a foam and pressurized with a liquefied or compressed propellant wherein the ratio of the foamable carrier to the propellant is about 100:1 to about 100:25.

In certain embodiments the Poloxamer comprises at least one of Poloxamer 124, Poloxamer 188, Poloxamer 237, Poloxamer 338 or Poloxamer 407 or mixtures of two or more thereof, such as 407 and 124. In a preferred embodiment the Poloxamer comprises at least one of Poloxamer 188 and Poloxamer 407 or mixtures thereof. In another embodiment the Poloxamer capable of fixing the composition, such as, Poloxamer 407. In an aspect the Poloxamer is about 0.2% to about 2% by weight. In different embodiments the Poloxamer comprises a molecular weight in a range (i) between about 2,000 and about 2,400; or (ii) between about 6,800 and about 8,900; or between about 7,600 and about 9,500; or (ii) between about 9,800 and about 14,600; or (iii) between about 12,000 and about 18,000. In certain aspects the ratio of Poloxamer to non ionic surface active agent is about 1:2; about 1:1; about 2:1; about 4:1; about 8:1; about 10:1; about 15:1; about 20:1; about 30:1; about 40:1; about 50:1, or any range or combination thereof (e.g., from about 1:2 to about 50:1; from about 1:1 to about 1:50; from about 2:1 to about 50:1; from about 4:1 to about 50:1; from about 8:1 to about 50:1; from about 10:1 to about 50:1; from about 15:1 to about 50:1; from about 20:1 to about 50:1; from about 30:1 to about 50:1; from about 40:1 to about 50:1; from about 1:2 to about 1:1; from about 1:2 to about 2:1; from about 10:1 to about 50:1; from about 2:1 to about 8:10; etc.). In other aspects, the ratio of Poloxamer to polymer or polysaccharide is from about 1:1 to about 50:1 (e.g., from about 1:2 to about 50:1; from about 1:1 to about 1:50; from about 2:1 to about 50:1; from about 4:1 to about 50:1; from about 8:1 to about 50:1; from about 10:1 to about 50:1; from about 15:1 to about 50:1; from about 20:1 to about 50:1; from about 30:1 to about 50:1; from about 40:1 to about 50:1; from about 1:2 to about 1:1; from about 10:1 to about 50:1; from about 2:1 to about 8:10; etc.).

In one or more embodiments the viscosity of the composition at about body temperature is substantially greater than the viscosity of the composition at room temperature.

In certain aspects, the percentage by weight of polyoxyethylene component of the poloxamer is between about 70% and about 85% of the Poloxamer.

In some embodiments, the foam produced has a mild cooling effect or sensation. Without being bound by a theory it is thought that the propellant can either be trapped to some extent in the polymeric spaces or network of the formulation or in the gel and when the expelled foam is applied to the skin some residual evaporation takes place.

In one or more embodiments the Poloxamer formulation aids the intradermal penetration of the active agent so that it is in excess of about 300 micrograms/cm$^2$/24 hr.

In one or more embodiments the Poloxamer improves the absorption of the active agent into the stratum corneum and thereafter into the dermis without a substantial increase in transdermal penetration.

In one or more embodiments the Poloxamer is included in the formulation in an amount sufficient to dissolve an active agent in an aqueous phase, wherein such an active agent is not fully soluble in said aqueous phase.

In one or more embodiments when the active agent is not otherwise fully soluble in water, in hydrophobic solvent, or in the oil phase of the emulsion, the Poloxamer is present in the composition in an amount sufficient to solubilize the active agent in the composition.

In one or more embodiments the active agent comprises at least one of diclofenac, salicylic acid or clindamycin or mixtures of two or more thereof.

In one or more embodiments the active agent in an effective amount is capable of causing the composition to form a gel, which in the presence of a sub effective amount would be liquid. For example salicylic acid can cause Poloxamer to gel In one or more embodiments the gelling effect is a result of a reduction in pH and or an increase of ionic strength.

In an aspect there is provided a Poloxamer composition, further comprising at least one ingredient, comprising:
  a. about 1% to about 50% of a hydrophobic solvent;
  b. about 1% to about 50% of a non-volatile hydrophilic solvent;
  c. about 0.01% to about 5% of a foam adjuvant; or
  d. about 1% to about 10% of a volatile hydrophilic solvent or mixtures of two or more thereof.

In an aspect there is provided a foamable Poloxamer composition further comprising a foam adjuvant comprising a fatty alcohol having 15 or more carbons in their carbon chain; or a fatty acid having 16 or more carbons in their carbon chain; or fatty alcohols, derived from beeswax and including a mixture of alcohols, a majority of which has at least 20 carbon atoms in their carbon chain; or a fatty alcohol having at least one double bond; a fatty acid having at least one double bond; or a branched fatty alcohol; or a branched fatty acid or a fatty acid substituted with a hydroxyl group or mixtures of two or more thereof.

In an aspect the Poloxamer formulation is an oil in water emulsion.

In an aspect there is provided a Poloxamer pharmaceutical or cosmetic cell composition comprising:
  a. water;
  b. a surfactant polymer system comprising a Poloxamer at a concentration of about 0.1 to about 20%;
  c. a therapeutic cell or a fragment or fraction thereof; and
wherein the Poloxamer is in an amount capable of forming a gel, upon exposure to body temperature, either alone or in combination with the supporting agent, wherein the supporting agent comprises about 0.1% to about 0.5% surface active agent, or about 0.1% to about 1% polymer or polysaccharide or mixtures thereof. In a certain embodiment the cell composition is foamable and wherein the composition is packaged in a canister comprising an aerosol container, equipped with a valve and an actuator, capable of releasing a foam and pressurized with a liquefied or compressed propellant at a concentration of about 1% to about 25% by weight of the total composition wherein the ratio of the foamable carrier to the propellant is 100:10 to 100:35;

In an aspect there is provided a Poloxamer composition which is suitable as a cell therapy composition comprising:
a. an aqueous solution, suitable to maintain therapeutic cells in viable state;
b. a Poloxamer/polymer system, comprising:
  i. about 20% a Poloxamer; or
  ii. a combination of (1) up to about 5% a Poloxamer; and (2) a polymeric agent or polysaccharide, wherein the polymeric agent or polysaccharide is added in an amount which, by itself, is not sufficient to produce a gel;
c. therapeutic cells;
or
a Poloxamer composition which is suitable as a cell therapy composition comprising:
a) an aqueous solution, suitable to maintain therapeutic cell fractions or fragments or mixtures of therapeutic cells and therapeutic cell fractions or fragments in a viable state;
b) a Poloxamer/polymer system, comprising:
  i. about 20% of a Poloxamer; and
  ii. a combination of (i) up to about 5% of a Poloxamer; and (2) a polymeric agent or polysaccharide, wherein the polymeric agent or polysaccharide is added in an amount which, by itself, is not sufficient to produce a gel;
c) therapeutic cell fractions or fragments alone or in combination with therapeutic cells.

In one or more embodiments any one or more of the Poloxamer cell formulations further comprises an active agent.

In one or more particular embodiments where an active agent is provided in the carrier formulation the active agent can be encapsulated, for example in a microsponge or any other of the encapsomes described below In another aspect there is provided pharmaceutical or cosmetic foamable composition for application to a delivery site in a subject, the composition comprising:
a. about 0.1% to about 20% by weight of at least one poloxamer;
b. 0% to about 5% by weight of at least one polymeric agent;
c. about 85% to about 99.8% water;
d. 0% to about 5% by weight of at least one silicone;
e. 0% to about 5% by weight of at least one surfactant;
f. 0% to about 15% by weight of at least one active agent, which optionally may be encapsulated; and
g. a propellant at a concentration of about 3% to about 25% by weight of the total aqueous foamable composition, wherein the composition is stored in an aerosol container and upon release expands to form a short term breakable stable foam.

In one or more embodiments the poloxamer and the polymeric agent or polysaccharide when present together act synergistically so that the amount of poloxamer required can be substantially reduced.

In one or more embodiments the polymeric agent or polysaccharide is water soluble or water dispersible.

In one or more embodiments the composition comprises about 95-99.8% water.

In one or more embodiments said at least one water-soluble or water dispersible polymeric agent or polysaccharide comprises one or more of a an acrylic acic polymer, a permulen, a carbomer, methocel, sodium CMC, PVP and xanthan gum.

In one or more embodiments said at least one silicone compound comprises one or more of cyclomethicone, dimethicone, cyclomethicone and dimethicone Copolyol (DC3225C).

In one or more embodiments the Poloxamer foam has a density of between about 0.01 to about 0.2 g/cm$^3$ In one or more limited embodiments the Poloxamer foam has a density in excess of about 0.2 g/cm$^3$ and the foam can takes the form of an aerated gel upon application to a delivery site, wherein the delivery site comprises skin or a body cavity.

In an aspect there is provided pharmaceutical or cosmetic foamable composition for application to a delivery site in a subject, the composition comprising:
a. about 5% to about 20% by weight of at least one poloxamer;
b. about 85% to about 99.8% water;
c. about 0.2% to about 15% by weight of at least one hydrophobic solvent;
d. about 0.5% to about 5% by weight of at least one surfactant;
e. about 0.5% to about 15% by weight of at least one hydrophilic solvent;
f. an active agent, which optionally may be encapsulated; and
g. a propellant at a concentration of about 3% to about 25% by weight of the total aqueous foamable composition, wherein the composition is stored in an aerosol container and upon release expands to form a short term breakable stable foam.

In an embodiment the hydrophobic solvent comprises a silicone. In an embodiment the hydrophobic solvent further comprises an oil. In an embodiment the hydrophilic solvent comprises a glycol. In an embodiment the hydrophilic solvent comprises glycerin. In an embodiment the hydrophilic solvent comprises a glycol and glycerin. When the Poloxamer composition comprises a silicone, a glycol and glycerin the intradermal penetration of the active agent can be in excess of about 300 micrograms/cm$^2$/24 hr.

In an embodiment the Poloxamer improves the absorption of the active agent into the stratum corneum and thereafter into the dermis without a substantial increase in transdermal penetration.

In an embodiment there is provided a method of treating, alleviating or preventing a disorder of a mammalian subject in need thereof, comprising administering a therapeutically effective amount of a pharmaceutical Poloxamer composition comprising an active agent or therapeutic cells or fragments thereof, to an afflicted target site of said mammalian subject.

In an embodiment there is provided method of treating, alleviating or preventing a disorder of a mammalian subject in need thereof, comprising administering a therapeutically effective amount of a foam produced from a Poloxamer composition comprising an active agent or therapeutic cells or fragments thereof, to an afflicted target site of said mammalian subject.

In one or more embodiments the propellant is separate from the formulation.

In one or more embodiments the composition is packaged in a dual chamber device having two canisters connected to a mixing means arranged and adapted to mix the contents of the canisters upon simultaneous release of their content, wherein the aqueous Poloxamer surfactant system is stored in a first canister and the aqueous therapeutic cells are packaged in a second canister wherein the surfactant system and the therapeutic cells are capable of being mixed upon being expelled from the canisters; and wherein the propellant in the second canister is separate from the therapeutic cells.

In one or more embodiments the dual chamber device has a metered dose means for each canister.

In one or more embodiments there is provided a method of treating, alleviating or preventing a disorder of a mammalian subject in need thereof, comprising administering a therapeutically effective amount of a gel or foam produced from a Poloxamer composition of claim 1 to an afflicted target site of said mammalian subject.

In one or more embodiments there is provided a Poloxamer composition having the following properties:
  a. a viscosity of about 1 to about 16,000 cP measured at ambient temperature; or
  b. a stability or resistance to centrifugation for ten minutes at about 3000 rpm; and wherein the resultant foam has at least 5 of the following properties:
  a. a density between about 0.01 and 0.2 g/cm$^3$;
  b. a pH of 3-7;
  c. a hardness of about 10 to 80 g;
  d. a texture of a very fine creamy foam consistency to a fine bubble structure consistency;
  e. a relatively short drainage time;
  f. a collapse time in excess of 180 secs;
  g. a collapse time in excess of 300 secs; and
  h. a sustainability of more than 95% for at least one minute a upon release thereof to the delivery site.

In one or more embodiments the Poloxamer composition has one property and the foam has 6 or 7 or all the properties. In one or more embodiments the composition has both properties. In one or more further embodiments the resultant foam has 6 or 7 or all of the properties.

One key element is the Poloxamer polymeric agent used in the formulation. Another contributing factor can be the additional presence of a polymer or polysaccharide. These polymeric agent(s) can contribute to the stability and stabilization of the formulation. Concentrations of polymeric agents and other thickeners have in the past been used to achieve very high viscosities of at least 20,000 cps to a million or more cps. Surprisingly, it has been unexpectedly found that by using low viscosities of the order of about 16,000 cps or less to about 1 cps, or less than about 10,000, or less than about 8000, or less than about 6000, or less than about 4000, or less than about 2000, or less than about 1000, for the pre foam formulation whose viscosity can be further reduced upon inclusion of propellant it has been possible to achieve a stable formulation that produces breakable foam of quality. It is unexpected that a hydrophilic highly aqueous formulation can provide Without being bound by any theory it may be the case that the polymeric agent(s) can provide an infrastructure or network around the propellant that unexpectedly is able to trap some propellant and or propellant is trapped in a gel or semi gel composition such that when the composition is released from a pressurized canister a quality form is released with good dispensing. This possibility is suggested by the observation that certain formulations when expelled provides a foam, which when applied immediately to a skin surface causes a mild cooling sensation, which may be due to propellant escape from the polymer network Moreover, the composition is able to stabilize the active agent physically and chemically.

In one or more embodiments an emulsion Poloxamer composition is provided comprising a silicone. Unexpectedly it is possible to make compositions which are flowable in which the propellant forms part of the oil phase of the emulsion formulation but nevertheless surprisingly does not make the formulation substantially vulnerable to phase separation and or sedimentation. Moreover these compositions are stable and are able to form breakable foam of quality that spreads easily and is able to deliver an effective and measurable amount of active agent homogeneously to a target surface. By introducing an oil shakability is improved.

In one or more embodiments the active agent is dissolved in the composition and is dissolved in the expelled foam.

BRIEF DESCRIPTION OF THE DRAWINGS

The invention is described with reference to the figures which are presented for the purpose of illustration and are not intended to be limiting.

DESCRIPTION

Figure 1:
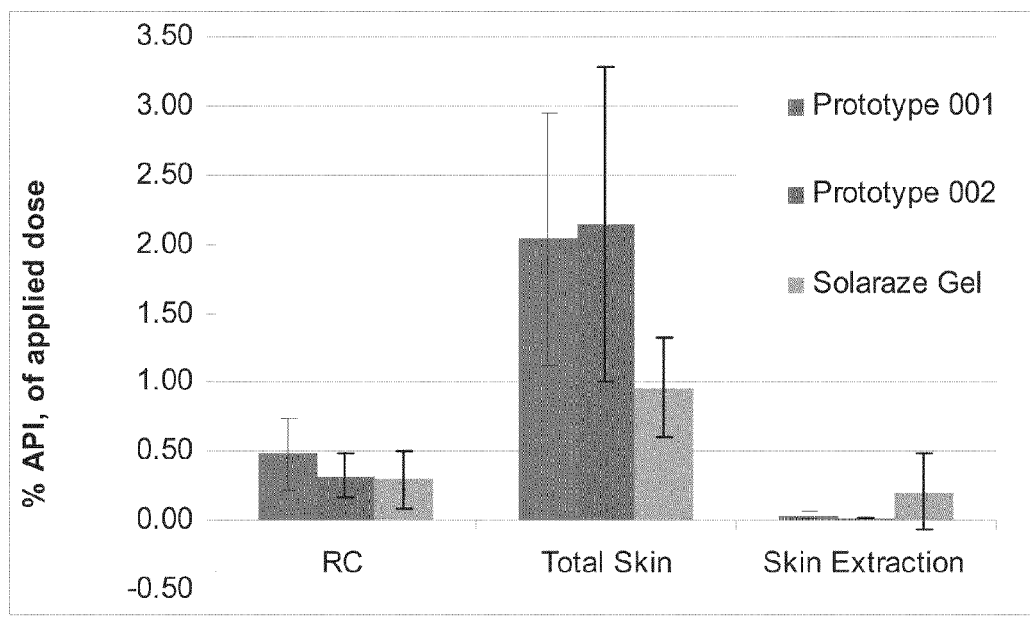
FIG. 1 is a bar chart showing Penetration of Diclofenac (mean values, % of applied dose) in different compositions.

This invention relates to foamable pharmaceutical and cosmetic vehicles or carriers; therapeutic compositions with active agents, therapeutic compositions where the active agent is encapsulated, for example, in microspheres, and delivery systems including cell delivery systems, comprising a Poloxamer.

In one or more embodiments no surfactant other than Poloxamer is required to make a gel or foam. The gel may be fixing such that it is liquid at room temperature and gel or semi gel like at or approaching body temperature, even at very low Poloxamer concentrations. In other embodiments other surfactants may be present. In further embodiments a combination of Poloxamer and polymer can be used.

There are provided polymer-based aqueous foams, especially very low density foams, where the main polymeric component is a Poloxamer and the foamable formulations include an active agent and are suitable for pharmaceutical or cosmetic administration with one or more propellants such that the resultant foams are easy to use, stable and non-irritating, with unique therapeutic properties which may include anti-infective properties and membrane transport properties. There are also provided such compositions in which the viscosity increases when the formulation is exposed to body temperature.

One important feature of topical products is the ability to deliver an effective amount of active agent intradermally with minimal transdermal penetration; and there are provided Poloxamer formulations with active agents, which provide improved intradermal penetration without significant transdermal penetration of such active agents.

An important feature of topical products is the solubility of active agents in the components of the composition and in the formulation as a whole. For example, the solubility can affect the rate of delivery of the active agent into the target site of treatment (such as the skin); and through membranes (such as the skin or mucosal membranes). There are provided formulations in which the Poloxamer improves the solubility of or acts to dissolve an active agent in an aqueous phase, wherein such an active agent is not fully soluble in said aqueous phase.

An important feature of topical products is the feel or sensation of the composition on application and there are provided Poloxamer based formulations which provide a mild cooling sensation without using large amounts of propellant.

There are provided new, improved, convenient to use, stable foam Poloxamer formulations, containing specific ingredients, which should effectively deliver and/or deposit various active agents into and onto the skin and/or other target sites and are relatively non-irritating and thus suitable for use by people having sensitive skin, mucosal areas and eyes.

According to one or more embodiments, the foamable composition includes the following essential components:
  a. water;
  b. a Poloxamer/surfactant system, selected from the group consisting of:
    i. about 5% to about 20% of Poloxamer; and
    ii. a combination of (i) about 0.1% to about 5% of a Poloxamer; and (2) a non-ionic surface active agent, and
  c. an active agent.

According to one or more embodiments, there is provided a pharmaceutical or cosmetic composition comprising:
  a. water;
  b. a surfactant/polymer system comprising a Poloxamer at a concentration of about 0.1 to about 15%;
  c. an active agent.

According to one or more embodiments, there is provided a foamable or pharmaceutical or cosmetic composition, wherein the active agent is provided in microspheres, which are suspended in the composition.

In some embodiments, the concentration of Poloxamer is between about 0.1% to about 5% and the composition further includes a supporting agent, such as a non-ionic surface active agent. In some embodiments, the concentration of Poloxamer is between about 0.1% to about 5%; and the composition further includes a supporting agent such as a non surfactant polymer or polysaccharide. In some embodiments, such as when the composition includes a supporting agent, the Poloxamer is capable of the fixing the composition to a body surface.

In some embodiments, the composition is capable of forming a foam. For example, in some embodiments the composition is packaged in a packaging assembly. The assembly includes, for example, a container (e.g., an aerosol container), equipped with a valve and an actuator. Such assemblies are capable of releasing a foam and pressurized with a liquefied or compressed propellant. In some embodiments, the ratio of the foamable carrier to the propellant is about 100:1 to about 100:25.

According to one or more embodiments, there is also provided a pharmaceutical or cosmetic composition comprising:
  a. water;
  b. a surfactant polymer system comprising a Poloxamer at a concentration of about 0.1 to about 20%; and
  c. a therapeutic cell or a fragment or fraction thereof.

According to one or more embodiments, there is also provided an aqueous foamable composition for application to a delivery site in a subject, the composition comprising:
  a) about 0.1% to about 20% by weight of at least one poloxamer;
  b) 0% to about 5% by weight of at least one polymeric agent;
  c) about 85% to about 99.8% water;
  d) 0% to about 5% by weight of at least one silicone;
  e) 0% to about 5% by weight of at least one surfactant;
  f) 0% to about 15% by weight of at least one active agent optionally encapsulated; and
  g) a propellant at a concentration of about 3% to about 25% by weight of the total aqueous foamable composition, wherein the composition is stored in an aerosol container and upon release expands to form a short term breakable stable foam.

In some embodiments, the Poloxamer and the polymeric agent when present together act synergistically so that the amount of Poloxamer required can be substantially reduced.

In some embodiments, the Poloxamer is in an amount capable of forming, upon exposure to body temperature, a gel either alone or in combination with a supporting agent. In certain embodiments, the supporting agent is selected from the group consisting of about 0.1% to about 0.5% surface active agent, about 0.1% to about 1% non surfactant polymer or polysaccharide or mixtures thereof.

In a preferred embodiment the Poloxamer is about 0.2% to about 2% in combination with a supporting agent.

All % values are provided on a weight (w/w) basis.

In the context of the present invention, the term "fixing" means a viscosity change of a formulation containing Poloxamer upon a temperature change such that the viscosity of a preparation comprising Poloxamer substantially increases when the temperature changes from room temperature of about 20° C. to a temperature of about 30° C. or more. In some embodiments "fixing" may also be induced by a change in the pH or in the ionic strength of the said solution. One consequence of fixing is that a liquid or semi liquid formulation turns viscous enough to remain substantially in the same place when applied to a body surface. The term "fixing Poloxamer" relates to a Poloxamer, which is capable, subject to exposure of elevated temperature, change in pH or ionic strength, of affording a "fixing" effect.

In an embodiment the composition comprises a Poloxamer in combination with a polysacharide to produce a synergistic gelling effect. This is a unique advantage, which enables much lower amounts of Poloxamer and polysaccharide to be used to achieve a gelling effect. Thus, whilst Poloxamer alone (e.g. Poloxamer 407) or polysaccharide alone (e.g., xantham gum) can produce aqueous gels, higher amounts are required than the total amount when they are in combination. Since Poloxamer has surfactant like properties, its presence in low concentrations is advantageous, for example, when the active agent of the composition comprises a therapeutic cell (as defined hereinbelow), and the cells are sensitive to surfactants. In an embodiment, in order to attain the fixing property, the Poloxamer is selected such that the formulation may be liquid or semi liquid at room temperature but upon warming to hand or body temperature the viscosity increases. In an embodiment the increase in viscosity is sufficient to have a gelling effect or to increase the retention time at the site of application or to increase the collapse time of a foam derived from the Poloxamer formulation.

In an embodiment the composition is packaged in an aerosol container, equipped with a valve and an actuator, capable of releasing a foam and pressurized with a liquefied or compressed propellant at a concentration of about 1% to about 25% by weight of the total composition. In an alternative embodiment the composition is packaged in a bag in aerosol or bag in valve delivery system in which the composition is stored in a bag separate from the propellant.

The foam released from the container is light and cosmetically-elegant. It is not a "quick-breaking" foam that collapses upon exposure to skin temperature; but rather it is breaks down upon application of very low sheer force, such as very easy movement of the fingers over the treated area.

The composition can contain one or more additional formulation additives, which can serve various functional purposes, including but not limited to one or more of the following purposes:

1. improvement of the appearance of the foam;
2. improvement of the skin sensation following application of the composition to a target body site;
3. improvement of the spreadability of the formulation when applied to the skin;
4. Facilitating quick absorption of one or more elements of the formulation when applied to the skin;
5. stabilization of an emulsion or a suspension;
6. skin conditioning and/or hydration;
7. modification of the delivery of the active agent into the target site and/or through membranes;
8. maintain an appropriate environment for the active pharmaceutical ingredient and excipients so that they remain stable when stored for prolonged periods and which is also suitable for application to the target site or therapeutic cells;
9. maintain an appropriate environment for the therapeutic cells so that they remain viable when applied to the to the target site; and
10. prevent or minimize breakdown of active agents and excipients;

Thus, the composition may contain one or more additional formulation additives, as follows:

a. about 1% to about 50% of a hydrophobic solvent;
b. about 1% to about 50% of a non-volatile hydrophilic solvent;
c. about 0.01% to about 5% of a foam adjuvant;
d. about 1% to about 10% of a volatile hydrophilic solvent.

Poloxamer

In an embodiment, the carrier comprises a Poloxamer. Poloxamer is a synthetic block copolymer of ethylene oxide and propylene, having the general formula of:

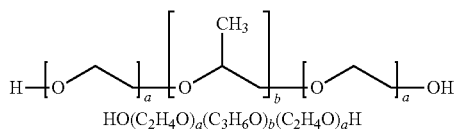

HO(C$_2$H$_4$O)$_a$(C$_3$H$_6$O)$_b$(C$_2$H$_4$O)$_a$H

For the generic term "Poloxamer", these copolymers are commonly named with the letter "P" (for Poloxamer) followed by three digits, the first two digits×100 give the approximate molecular mass of the polyoxypropylene core, and the last digit×10 gives the percentage polyoxyethylene content. For example, P407 is a Poloxamer with a polyoxypropylene molecular mass of 4,000 g/mol and a 70% polyoxyethylene content.

Poloxamers have several useful characteristics depending on the Poloxamer(s) selected. They can be thickeners and at higher concentrations gel forming in aqueous solution. They also have surfactant properties and can act as emulsifiers and wetting agents. Some are able to create thermo-sensitive solutions, such that their properties such as viscosity change with temperature. They are strongly hydrophilic and can help to improve solubility. Poloxamers are soluble in water and in alcohol. Poloxamers are used as emulsifying agents for intravenous fat emulsions, as solubilizing agents to maintain clarity in elixirs and syrups and as wetting agents for anti bacterials. They have been used in a variety of oral parenteral, and topical pharmaceutical formulations and are generally regarded as nontoxic and non irritant. Poloxamers are stable materials and aqueous solutions of Poloxamers are stable in the presence of acids, bases and metal ions. Poloxamers are not metabolized by the body.

Poloxamers are available in different grades which vary from liquids to solids. Table I, below exemplifies types of Poloxamers, conforming to the following requirements:

TABLE 1

| Poloxamer | Physical Form | Average Molecular Weight | Weight % Oxyethylene | Unsaturation mEq/g |
|---|---|---|---|---|
| 124 | Liquid | 2090-2360 | 46.7 ± 1.9 | 0.020 ± 0.008 |
| 188 | Solid | 7680-9510 | 81.8 ± 1.9 | 0.026 ± 0.008 |
| 237 | Solid | 6840-8830 | 72.4 ± 1.9 | 0.034 ± 0.008 |
| 338 | Solid | 12700-17400 | 83.1 ± 1.7 | 0.031 ± 0.008 |
| 407 | Solid | 9840-14600 | 73.2 ± 1.7 | 0.048 ± 0.017 |

Examples of other Poloxamers are: 181, 182, 183, 184, 185, 212, 215, 217, 231, 234, 235, 238, 331, 333, 334, 335, 401, 402, and 403.

The successful restoration of membrane transport properties through surfactant Poloxamer 188 has been demonstrated. Poloxamer 188 (P188, mol wt=8400 g/mol), has the structure of poly(ethylene oxide)-poly(propylene oxide)-poly(ethylene oxide) (PEO-PPO-PEO, with 80 wt % PEO content). As a result of its amphiphilic nature, P188 has the capability to interact with a cell membrane and is found to alleviate as well as reverse damages caused by electrical trauma.

In an embodiment, the Poloxamer is included in the formulation, in an amount between about 0.1% and about 30%, preferably between about 0.5% and about 25% or more preferably between about 1% and about 10%.

In an embodiment, the Poloxamer is included in the formulation in an amount sufficient to dissolve an active agent in an aqueous phase, wherein such an active agent is not fully soluble in said aqueous phase.

In addition of their unique formulation properties, Poloxamers possess certain therapeutic effects. For example, Poloxamer 188 has been reported to improve capillary blood flow in burn injury (J Surg Res. 2001; 101(1):56-61); and Poloxamer 407 possesses immunomodulation and cytotoxicity-promoting properties (Pharmaceutical Res. 2006; 23(12): 2709-2728). Poloxamers have been reported to have anti-mycobacterial activity within macrophages (Abstr Intersci Conf Antimicrob Agents Chemother Intersci Conf Antimicrob Agents Chemother). 1999 Sep. 26-29; 39:400) and they enhance the phagocytic activity of macrophases (Journal of the National Cancer Institute, Vol. 88, No. 11, Jun. 5, 1996). Thus, in certain embodiments, the Poloxamer acts not only as a formulation (vehicle) component, but also as an active agent of the composition, alone, or together with another active agent.

The sensory properties of foams containing a Poloxamer are favorable, as revealed by consumer panel tests.

It has been surprisingly discovered that Poloxamer 407 can be fixing at low levels of Poloxamer.

Surface-Active Agent

HLB

The composition may contain a surface-active agent in addition to Poloxamer. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In certain cases HLB values can be found outside the standard range.

In many cases a single Poloxamer or a combination of Poloxamers suffice to facilitate producing a foam. Similarly where a liquid or semi liquid formulation which becomes gel like is desired a single fixing Poloxamer or a combination of Poloxamers at least one of which is a fixing Poloxamer may suffice to achieve effective fixing. In one or more embodiments the combination of poloxamers or poloxamers and another polymer or polysaccharide may act synergistically.

In other cases a combination of a Poloxamer with one or more surfactants other than Poloxamer) is desired. As will be appreciated by a person skilled in the art which surfactant or surfactant system is more appropriate is related to the vehicle and intended purpose. It has been further discovered that the generally thought HLB considerations are not always binding and that good quality foams can be produced with a surfactant or surfactant combination both where the HLB values are in or towards the lipophilic side of the scale and also where the HLB values are in or towards the hydrophilic side of the scale.

According to one or more embodiments in addition to Poloxamer the composition contains a single surface active agent having an HLB value between about 2 and about 9, or more than one surface active agent and the weighted average of their HLB values is between about 2 and about 9. Lower HLB values may in certain embodiments be more applicable to water in oil emulsions.

According to one or more embodiments in addition to Poloxamer the composition contains a single surface active agent having an HLB value between about 7 and about 14, or more than one surface active agent and the weighted average of their HLB values is between about 7 and about 14. Mid range HLB values may, in certain embodiments, be more suitable for oil in water emulsions.

According to one or more other embodiments in addition to Poloxamer the composition contains a single surface active agent having an HLB value between about 9 and about 19, or more than one surface active agent and the weighted average of their HLB values is between about 9 and about 19.

According to one or more preferred embodiments the surface-active agent (other than Poloxamer) has a hydrophilic lipophilic balance (HLB) between about 9 and about 14, or the composition contains more than one surface active agent and the weighted average of their HLB values is between about 9 and about 14.

Non-Ionic Surfactants

In one or more embodiments, the surface-active agent in addition to Poloxamer includes at least one non-ionic surfactant. Ionic surfactants are known to be irritants. Therefore, non-ionic surfactants are preferred in applications including sensitive tissue such as found in most mucosal tissues, especially when they are infected or inflamed.

Non limiting examples of possible non-ionic surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene) alkyl ethers, such as poly(oxyethylene) cetyl ether, poly(oxyethylene) palmityl ether, polyethylene oxide hexadecyl ether, polyethylene glycol ether, brij 38, brij 52, brij 56, brij W1, ceteareth 20; sucrose esters, partial esters of sorbitol and its anhydrides, such as sorbitan monolaurate and sorbitan monolaurate; mono or diglycerides, isoceteth-20, and mono-, di- and tri-esters of sucrose with fatty acids (sucrose esters including those having high monoester content, which have higher HLB values).

Mixtures of Non-Ionic Surfactants are Contemplated

In one or more embodiments the surface active agent is a complex or combination of two or more surface active agents (one of which may be poloxamer) that can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex comprises a combination of surfactants wherein there is a difference of about 4 or more units between the HLB values of the two surfactants or there is a significant difference in the chemical nature or structure of the two or more surfactants.

Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect. Non limiting examples of surfactants with postulated tendency to form interfacial liquid crystals are: phospholipids, alkyl glucosides, sucrose esters, sorbitan esters. In certain embodiments surfactants which tend to form liquid crystals may improve the quality of foams produced from compositions.

In one or more embodiments, the surfactant in addition to Poloxamer is a surfactant or surfactant combination that is capable of or which tends to form liquid crystals.

In one or more embodiments, the at least one surface active agent is solid, semi solid or waxy.

Ionic Surfactants

In certain cases, the surface active agent is ionic and is selected from the group of anionic, cationic, zwitterionic, amphoteric and ampholytic surfactants, such as sodium methyl cocoyl taurate, sodium methyl oleoyl taurate, alkyltrimethylammonium salts, sodium lauryl sulfate, triethanolamine lauryl sulfate and betaines.

Combination of Non-Ionic and Ionic Surfactants

In additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1.

In one or more embodiments, a combination of a non-ionic surfactant and an ionic surfactant (such as an anionic surfactant sodium lauryl sulphate or a zwitterionic surfactant cocamidopropyl betaine) is employed, at a ratio of between 1:1 and 20:1, or at a ratio of 4:1 to 10:1. The resultant foam has a low specific gravity, e.g., less than 0.1 g/ml.

Where there is a combination of non-ionic and ionic surfactants then at least one non ionic surfactant is a Poloxamer.

The concentration of the surface active agent other than Poloxamer is between about 0.1% and about 5%. In a more preferred embodiment the concentration of surface active agent other than Poloxamer is between about 1% and about 4%.

Synergistic Foam Forming Effect

Surprisingly, it was found that while concentrations of less than about % or about 2% of a Poloxamer, are not sufficient to produce a composition that evolves an acceptable foam of quality, the addition of even small amounts of a non-ionic surface active agent affords an excellent foam with high expansion (density of less that 0.1 g/mL), easy spreadability and quick absorption into the skin upon application.

In an embodiment where there is a combination of (1) about 0.1% to about 5% of a Poloxamer; and (2) a non-ionic surface active agent, the ratio of Poloxamer to non ionic surface active agent is from about 1:2; about 1:1; about 2:1; about 4:1; about 8:1; about 10:1; about 15:1; about 20:1; about 30:1; about 40:1; to about 50:1.

In an embodiment where there is a combination of (i) about 0.1% to about 5% of a Poloxamer; and (2) an ionic surface active agent, the ratio of Poloxamer to ionic surface active agent is from about 1:2 to about 1:1; about 2:1; about 4:1; about 8:1; about 10:1; about 15:1; about 20:1; about 30:1; about 40:1; to about 50:1;

Hydrophobic Solvent

The foamable composition can be an emulsion, or microemulsion, including an aqueous phase and an organic carrier phase. In one or more embodiments the emulsion may comprise hydrophilic and hydrophobic ingredients combined in a predominately aqueous base, Thus, optionally, the foamable vehicle further includes at least one hydrophobic solvent, which constitutes the organic phase of the emulsion, at a concentration of about 1% to about 50% by weight. A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL. It is semi-solid or liquid at ambient temperature. The identification of a "hydrophobic solvent", as used herein, is not intended to characterize the solubilization capabilities of such solvent for any specific active agent or any other component of the foamable composition. Rather, such information is provided to aid in the identification of materials suitable for use as a hydrophobic component in the foamable compositions described herein. Examples of hydrophobic solvents include, but are not limited, to the following classes:

Triglycerides and Plant-Derived Oils

According to one or more embodiments, hydrophobic solvents are liquid oils originating from vegetable, marine or animal sources, which are usually triglycerides. Suitable liquid oils include partially-saturated, unsaturated or polyunsaturated oils. By way of non limiting example, the partially saturated or unsaturated oil may be olive oil, corn oil, soybean oil, canola oil, cottonseed oil, coconut oil, sesame oil, sunflower oil, borage seed oil, syzigium aromaticum oil, hempseed oil, herring oil, jojobo oil, cod-liver oil, salmon oil, flaxseed oil, wheat germ oil, evening primrose oils or mixtures thereof, in any proportion.

Capric/Caprylic Triglycerides are Commonly used in Topical Formulations

Unsaturated and polyunsaturated oils are oils that contain unsaturated and/or poly-unsaturated fatty acids such as oleic acid, linoleic acid, linolenic acid, gamma-linoleic acid (GLA), eicosapentaenoic acid, and docosahexaenoic acid. Oils containing such unsaturated and ply-unsaturated fatty acids are known for their therapeutic benefits when applied topically.

Esters of Fatty Acids

Esters of fatty acids, suitable for use as a hydrophobic solvent, include but are not limited to isopropyl palmitate, isopropyl isostearate, octyl palmitate, cetyl lactate, cetyl ricinoleate, tocopheryl acetate, cetyl acetate, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, Silicones Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenylsiloxane) copolymers. These are chosen from cyclic or linear polydimethylsiloxanes containing from about 3 to about 9, preferably from about 4 to about 5, silicon atoms. Volatile silicones such as cyclomethicones can also be used. Silicone oils are also considered as therapeutically active hydrophobic solvents, due to their barrier retaining and protective properties. In one or more embodiments, the hydrophobic carrier includes at least about 1%, about 2%, about 3%, about 4% by weight silicone oil or at least about 5% by weight.

Polypropylene Glycol Alkyl Ether

In an embodiment, the organic carrier is a polypropylene glycol alkyl ether (PPG alkyl ether). PPG alkyl ethers are liquid, water-insoluble propoxylated fatty alcohols, having the molecular formula of $RO(CH_2CHOCH_3)_n$; wherein "R" is a straight-chained or branched $C_4$ to $C_{22}$ alkyl group; and "n" is in the range between 4 and about 50. They are organic liquids that function as skin-conditioning agent in pharmaceutical and cosmetic formulations. Non-limiting exemplary PPG alkyl ethers include PPG stearyl ethers and PPG Butyl Ether. Preferred PPG alky ethers according to the present invention include PPG-15 Stearyl Ether, PPG-2 Butyl Ether, PPG-9-13 Butyl Ether and PPG-40 Butyl Ether.

Fatty Acids and Fatty Alcohols as Hydrophobic Solvents

In an embodiment, the hydrophobic solvent is a fatty acid which are liquid of semi-solid at ambient temperatures. Exemplary liquid or semi-solid fatty acids include, but are not limited to unsaturated fatty acids, polyunsaturated fatty acids and branched fatty acids. Examples of unsaturated fatty acids include myristoleic acid, palmitoleic acid and oleic acid. Examples of polyunsaturated fatty acids include linoleic acid, α-linolenic acid, arachidonic acid, eicosapentaenoic acid, erucic acid and docosahexaenoic acid. An example for branched fatty acids is isostearic acid, which is a clear, oily liquid.

In an embodiment, the hydrophobic solvent is a fatty alcohol which are liquid of semi-solid at ambient temperatures. Examples of liquid or semi-solid fatty alcohols include, but are not limited to unsaturated fatty alcohols, polyunsaturated fatty alcohols and branched fatty alcohols. Exemplary unsaturated fatty alcohols include cis-6-octadecen-1-ol (petroselenyl alcohol), cis-9-octadecen-1-ol (oleyl alcohol) and cis-11-octadecen-1-ol (vaccenyl alcohol). Exemplary of polyunsaturated fatty alcohols include bombykol (tr-10,cis-12-hexadecadien-1-ol), and avocadene (16-heptadecene-1,2, 4-triol). An example for branched fatty acids is isostearyl alcohol.

Mineral Oil and Petrolatum

Mineral oil (Chemical Abstracts Service Registry number 8012-95-1) is a mixture of aliphatic, naphthalenic, and aromatic liquid hydrocarbons that derive from petroleum. It is typically liquid; its viscosity is in the range of between about 35 CST and about 100 CST (at 40° C.), and its pour point (the lowest temperature at which an oil can be handled without excessive amounts of wax crystals forming so preventing flow) is below 0° C. In certain embodiments, the hydrophobic solvent comprises or contains petrolatum, which is also termed "white petrolatum" and "Vaseline". Petrolatum depending on the amount in a formulation and the nature of the formulation can form an impermeable occlusive layer, which protects the skin and may facilitate enhanced penetration of active agents.

Hydrophobic Waxes

In an embodiment, the hydrophobic solvent is a wax, selected from the group consisting of (1) a fatty alcohol; (2) a fatty acid; and (3) certain naturally occurring waxes. Examples of waxes, suitable as hydrophobic solvents in accordance to the present invention include, but are not limited, to (1) a C8 to C22 fatty acid or fatty alcohol; (2) C16 to C20 fatty acid or fatty alcohol; (3) a branched chain fatty acid or fatty alcohol; (4) a straight chain fatty acid or fatty alcohol; (5) a saturated fatty acid or fatty alcohol (6) an unsaturated fatty acid or fatty alcohol; (7) a fatty acid or a fatty alcohol, selected from the group consisting of isostearic acid, oleic acid, oleyl alcohol, stearic acid, cetyl alcohol, stearyl alcohol, erucic acid, linoleic acid, arachidonic acid and linolenic acid; (8) a fatty acid or a fatty alcohol, selected from the group consisting of lauric acid, myristic acid, palmitic acid, stearic acid, behenic acid, oleic acid, 12-hydroxystearic acid, undecylenic acid, tall acid, isostearic acid, linoleic acid, linolenic acid, eicosapentaenoic acid (EPA), docosahexaenoic acid (DHA); and (9) jojoba oil. In certain preferred embodiment, the wax is semi-solid or liquid at ambient temperature, such as oleyl alcohol, isostearic acid and jojoba oil.

Essential Oils

Essential oils are plant oils extracted by distillation. Non-limiting examples of essential oils include agar oil, ajwain oil, angelica root oil, anise oil, balsam oil, basil oil, bergamot oil, black Pepper essential oil, buchu oil, cannabis flower essential oil, caraway oil, cardamom seed oil, carrot seed oil, cedarwood oil, chamomile oil, cinnamon oil, cistus, citronella oil, clary Sage, clove leaf oil, coriander, costmary oil, cranberry seed oil, cumin oil/Black seed oil, cypress, davana oil, dill oil, eucalyptus oil, fennel seed oil, fenugreek oil, frankincense oil, galbanum, geranium oil, ginger oil, grapefruit oil, henna oil, jasmine oil, juniper berry oil, lavender oil, lemon oil, lemongrass oil, litsea cubeba oil, melissa oil (Lemon balm), mentha arvensis oil/Mint oil, mugwort oil, mustard oil, myrrh oil, neroli oil, orange oil, oregano oil, orris oil, parsley oil, patchouli oil, perilla essential oil, pennyroyal oil, peppermint oil, pine oil, rose oil, rosehip oil, rosemary oil, rosewood oil, sassafras oil, savory oil, schisandra oil, spearmint oil, star anise oil, tarragon oil, tea tree oil, thyme oil, vetiver oil, yarrow oil and ylang-ylang oil. Many essential oils are used as medical and aromatherapy applications, and thus, can be considered as therapeutically active hydrophobic solvents.

Emollients and "Therapeutically Active Hydrophobic Solvents"

Emollients are substances that soften and soothe the skin. They are used to correct dryness and scaling of the skin. Many of the hydrophobic solvents listed herein possess emollient properties and therefore, in addition to their contribution to the formulation texture, they provide an extra-benefit in the treatment of damaged skin and skin afflicted by a disorder that involves dry skin (such as psoriasis and atopic dermatitis).

Certain hydrophobic solvents listed herein further possess other properties which, which contribute to the therapeutic benefit of the present foamable composition, such as antibacterial, antifungal and anti-inflammatory properties. In the context, oils that possess therapeutically-beneficial properties are termed "therapeutically active solvent".

Mixtures of various hydrophobic solvents are anticipated.

Polar Solvent

Optionally, the foamable vehicle further includes at least one polar solvent. A "polar solvent" is an organic solvent, typically soluble in both water and oil. Polar solvents, such as detailed below possess high solubilizing capacity and contribute to the skin penetration of an active agent. Examples of polar solvents include dimethyl isosorbide polyols, such as glycerol (glycerin), propylene glycol, hexylene glycol, diethylene glycol, propylene glycol n-alkanols, terpenes, di-terpenes, tri-terpenes, limonene, terpene-ol, 1-menthol, dioxolane, ethylene glycol, other glycols, oleyl alcohol, alpha-hydroxy acids, such as lactic acid and glycolic acid, sulfoxides, such as dimethylsulfoxide (DMSO), dimethylformamide, methyl dodecyl sulfoxide, dimethylacetamide, azone (1-dodecylazacycloheptan-2-one), 2-(n-nonyl)-1,3-dioxolane, alkanols, such as dialkylamino acetates, and admixtures thereof. In certain preferred embodiments, the polar solvent is selected from the group consisting of dimethyl isosorbide glycerol (glycerin), propylene glycol, hexylene glycol, terpene-ol, oleyl alcohol, lactic acid and glycolic acid.

According to one or more embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Hydrophilic Emollients and "Therapeutically Active Solvents"

Certain hydrophilic solvents listed herein, such as glycerin, various glycols (for example propylene glycol_), α-hydroxy acids and PEGs (for example PEG, 200, 400, 600, 4000, 6000, 10,000) attract water and consequently possess emollient properties and therefore, in addition to their contribution to the formulation texture, they provide an extra-benefit in the treatment of damaged skin and skin afflicted by a disorder that involves dry skin (such as psoriasis and atopic dermatitis).

Certain hydrophobic solvents listed herein such glycerin, various glycols (for example propylene glycol), α-hydroxy acids, further possess other properties which, which contribute to the therapeutic benefit of the present foamable composition, such as antibacterial, antifungal, anti-inflammatory properties, anti-psoriasis and anti-aging effects. In the context, hydrophilic solvents that possess therapeutically-beneficial properties are termed "therapeutically active solvent".

Non-limiting examples of alpha hydroxy acids include glycolic acid, lactic acid, malic acid, citric acid, alpha-hydroxyethanoic acid, alpha-hydroxyoctanoic acid, alpha-hydroxycaprylic acid, hydroxycaprylic acidglycolic acid, tartaric acid, pyuric acid, citric acid, as well as their corresponding salts and pharmaceutically-acceptable derivatives; or any combination of any of the foregoing.

Hydroxy acids can help solubility and dermal penetration of a variety of drugs or cosmetic active agents.

Polysacharides/Celluloses/Glucans/Other Polymers

"Polysaccharides" refer to agents which contain a backbone of repeating sugar (i.e., carbohydrate) units. Nonlimiting examples of polysaccharide gelling agents include xantham gum, agar, guar gum, locust bean gum, sodium alginate, sodium caseinate, gelatin agar, carrageenin gum, sodium alginate, xanthan gum, tragacanth gum, cationic guars, hydroxypropyl guar gum, starch, a chemically modified starch, hydroxypropyl starch, hyaluronic acid, sodium hyaluronate, sodium stearyl fumarate, chitosan, ceratonia, pectin, calcium alginate, alginic acid, carrageenan and the like and those selected from cellulose, carboxymethycellulose sodium (NaCMC), carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, methylhydroxypropylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a C10-C30 straight chain or branched chain alkyl group through an ether linkage. Typically these polymers are ethers of CloC30 straight or branched chain alcohols with hydroxyalkylcelluloses. Examples of alkyl groups useful herein include those selected from stearyl, isostearyl, lauryl, myristyl, cetyl, isocetyl, cocoyl (i.e. alkyl groups derived from the alcohols of coconut oil), paln-lityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol O CS Plus from Aqualon Corporation (Wilmington, Del.). Other useful polysaccharides include scleroglucans which are a linear chain of (1-3) linked glucose units with a Q-6) linked glucose every three units, a commercially available example of which is Clearogel™ CS 11 from Michel Mercier Products Inc. (Mountainside, N.J.).

Other useful polymeric agents include a carboxyvinyl polymer, polyvinylpyrrolidone, polyvinyl alcohol, a polyacrylic acid polymer, a polymethacrylic acid polymer, acrylates/C10-C30 alkyl acrylates cross polymer, polyvinyl acetate, a polyvinyl chloride polymer, a polyvinylidene chloride polymer, a cationic cellulose, polyvinylpyrrolidone (PVP), PEG 1000, PEG1500, PEG2000, PEG 4000, PEG 6000, PEG 8000, a polycarbophil, a carbomer, ASOS, and a pemulen. Some polymers are sensitive to pH like carbomers and may be used with a weak base such as trolamine (also known as triethanolamine or TEA) to aid or control their expansion.

It is thought that the polysaccharides and the other useful polymers act as stabilizers and thickeners. They are not considered surfactants except perhaps for pemulen, which can act as a non traditional emulsifier.

In an embodiment where there is a combination of (i) about 0.1% to about 5% of a Poloxamer; and (2) a non-ionic polymer or polysacharide, the ratio of Poloxamer to non ionic polymer or polysacharide is from about 1:1; about 2:1; about 4:1; about 8:1; about 10:1; about 15:1; about 20:1; about 30:1; about 40:1; to about 50:1;

Foam Adjuvant

Optionally, the foamable vehicle further includes a foam adjuvant selected from the group consisting of a fatty alcohol, which is solid at ambient temperature, having 15 or more carbons in their carbon chain; a fatty acid including straight-chain fatty acids, branched and substituted fatty acids, which is solid at ambient temperature, having 16 or more carbons in their carbon chain.

Additional Components

In an embodiment of the composition includes one or more additional components. Such additional components include but are not limited to one or more antioxidants, anti perspirants, anti-static agents, buffering agents, bulking agents, chelating agents, cleansers, colorants, conditioners, deodorants, diluents, dyes, emollients, flavanoids, fragrances, hair conditioners, humectants, ionization agents, moisturizers, occlusive agents, perfuming agents, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

Preservatives, Anti-Oxidants/Radical Scavengers, Ionizing Agents, Buffering Agents and pH Modifying Agents In one or more embodiments, the composition contains a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox$^R$), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

In one or more embodiments the antioxidant agent is a flavonoid. A non limiting list of flavonoid compounds is: benzquercin, diosmin, ethoxazorutoside, flavodate, sodium hesperidin, leucocianido, monoxerutin, oxerutin, quercetin, rutoside, rutin, rosmarinic acid.

Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In one or more embodiments of the present invention, a chelating agent is selected from the group consisting of acetyl trihexyl citrate, aminotrimethylene phosphonic acid, beta-alanine diacetic acid, bismuth citrate, EDTA and salts thereof, HEDTA and salts thereof, citric acid, cyclohexanediamine tetraacetic acid, diammonium citrate, dibutyl oxalate, diethyl oxalate, diisobutyl oxalate, diisopropyl oxalate, dilithium oxalate, dimethyl oxalate, dipotassium edta, dipotassium oxalate, dipropyl oxalate, disodium pyrophosphate, etidronic acid, methyl cyclodextrin, oxalic acid, pentapotassium, triphosphate, pentasodium aminotrimethylene phosphonate, pentasodium pentetate, pentasodium triphosphate, pentetic acid, phytic acid, potassium citrate, sodium citrate, sodium dihydroxyethylglycinate, sodium gluceptate, sodium gluconate, sodium hexametaphosphate, sodium metaphosphate, sodium metasilicate, sodium oxalate, sodium trimetaphosphate, tetrahydroxypropyl ethylenediamine, tetrapotassium etidronate, tetrapotassium pyrophosphate, tetrasodium etidronate, tetrasodium pyrophosphate, trisodium phosphate, malic acid, fumaric acid, maltol, succimer, penicillamine, dimercaprol, and desferrioxamine mesilate. Other authorized chelating agents are listed pursuant to annex 1, paragraph E.3.1 of regulation (EC) No 2003 (See Directive 67/548/EEC OJ 196, 16.8 1967, p 1) and are also incorporated herein by reference.

Humectants/Moisturisers

A humectant, is a substance that helps retain moisture and also prevents rapid evaporation. Non limiting examples of suitable heumectants are propylene glycol, propylene glycol derivatives, and glycerin. Further humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

Other examples of humectants and moisturizers may be found in the Handbook of Pharmaceutical Additives published by Gower. Suitable ones for use with and soluble in the waterless compositions of the present invention may be selected as will be appreciated by a person skilled in the art.

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Glycerine and sodium pCA work in combination. Other examples may be found in the Handbook of Pharmaceutical Additives published by Gower.

Pharmaceutical compositions of the present invention may in one or more embodiments usefully comprise in addition a humectant or a moisturizer or combinations thereof.

Propellant

In an embodiment, the propellant is a hydrocarbon propellant. Examples of suitable hydrocarbon propellants include volatile hydrocarbons such as butane, propane, isobutane or mixtures thereof. Non limiting examples are AP70; AP46; and 1681. Alternatively, use of ether propellants, fluorocarbon propellants, as well as compressed gases (e.g., air, carbon dioxide, nitrous oxide, and nitrogen) is also possible. Examples of other optional propellants are dimethyl ether (DME), methyl ethyl ether and hydrofluoroalkanes (HFA), for example HFA 134a (1,1,1,2-tetrafluoroethane) and HFA 227 (1,1,1,2,3,3,3-heptafluoropropane). Mixtures of propellants can be useful. Typical concentrations of hydrocarbon and fluorocarbon propellants is between about 3% and about 25%, however, in various applications, higher concentrations, up to about 40% or in limited cases even up to about 70% can be used. The concentration of a compressed gas, such as carbon dioxide and nitrogen is restricted to up to about 5% to 10% due to their high pressure; however, it should be noted that even about 1% propellant depending upon the pressure and formulation may be sufficient to evolve a foam. In an embodiment, the ratio of the foamable carrier to the propellant is about 100:1 to about 100:25.

Composition and Foam Physical Characteristics and Advantages

A pharmaceutical or cosmetic composition manufactured using the foamable carrier is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable Poloxamer compositions are stable, such that they are capable of having an acceptable shelf-life of at least about six months, preferably about one year, or more preferably, at least about two years at ambient temperature The aqueous Poloxamer foams demonstrate desirable texture; they form fine bubble structures that do not break immediately upon contact with a surface, spread easily on the treated area and absorb quickly.

The foamable composition should also be able to flow through the aperture of the container, e.g., aerosol valve and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

Density is also a distinguishing factor in looking at the quality of foams. Poloxamers are used herein to form low density foams with good expansion having a density of less than about 0.2 g/ml, preferably with a density of less than about 0.1 g/ml. Where the Poloxamer formulations have a density of more than about 0.2 g/ml they do not form true foams and are considered to be aerated or bubble gels, being formed by expulsion with a propellant from a sealed canister under ambient conditions. Foam quality grading as above is not really appropriate for bubble gels which are mentioned herein since the bubble gel is not a foam or not a true foam and displays relatively high density (about 0.2 to about 0.9 $g/cm^3$), much less expansion and slow drainage.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

The breakable foam herein is not "quick breaking" and is not "thermolabile", i.e., it does not collapse quickly upon expulsion and it does not readily collapse or melt upon exposure to body temperature environment. The breakable foam further does not display a long delayed expansion over minutes. Stability over a short time frame of minutes has advantages over foam which collapses quickly upon release. Similarly sheer-force breakability of the foam is clearly advantageous over thermally induced breakability. Both these factors allow for comfortable application and well directed administration to the target area. Breakable foam can break readily upon the application of shear force such as gentle rubbing to spread easily over a target surface. The sheer-force breakable foams herein are of low density, which further assists spreadability and contributes to a light pleasant feel. In certain embodiments the breakable foam is also fixing.

Another property of the foam is specific gravity, as measured upon release from the aerosol can. Typically, Poloxamer foams have specific gravity of less than about 0.2 g/mL; or less than about 0.12 g/mL; or less than about 0.10 g/mL; or less than about 0.08 g/mL, depending on their composition and on the propellant concentration.

According to certain embodiments, the foamable composition is alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. This disadvantage is particularly meaningful in the case of an antibiotic treatment, which is often directed to open wounds and damaged skin and mucosal tissues. In one or more other embodiments, the composition is substantially alcohol-free and includes less than about 5% final concentration of lower alcohols, preferably less than about 2%, more preferably less than about 1%.

Pharmaceutical Composition

The foamable carrier is an ideal vehicle for active pharmaceutical ingredients and active cosmetic ingredients. In the context, active pharmaceutical ingredients and active cosmetic ingredients are collectively termed "active agent" or "active agents".

Suitable Active Agents

Suitable active agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers. As is known to one skilled in the art, in some instances a specific active agent may have more than one activity, function or effect.

Encapsulation of an Active Agent

In one or more embodiments, the active agent is encapsulated. The encapsulation may be, for example, in particles, microparticles, nanoparticles, microcapsules, microspheres, nanocapsules, nanospheres, liposomes, niosomes, polymer matrix, mineral bodies, silica-gel, graphite, nanocrystals, dendrimers or microsponges. Such particles etc., (hereinafter "encapsome") can have various functions, such as (1) protection of the drug from degradation; (2) modification of the drug release rate from the composition; (3) control of skin penetration profile; and (4) mitigation of adverse effects, due to the controlled release of the active agent from the encapsulation particles.

An "encapsome" may be used to incorporate one or more active agents in a gel or foam. For example, it may retain within its structure or confines at least one active agent during storage, and yet release active agent at the delivery site responsive to a local temperature effect, a local pH effect, a local conductivity effect or any other local parameter or stimulus of the delivery site, which is different from that of the storage conditions.

Microsponges are macroporous beads, typically 10-25 microns in diameter, loaded with active agent. They consist of a copolymer, such as methyl methacrylate/glycol dimethacrylate crosspolymer. Examples of drugs that have been incorporated in microsponges include ibuprofen ketoprofen (non-steroidal anti-inflammatory agent), benzyl peroxide (an anti-acne agent), and fluconazole (an antifungal agent). Microsponges on application to skin release the active ingredient on a time mode and also in response to other stimuli (rubbing, temperature, pH, etc). In one or more embodiments microsponges may be incorporated into the formulations exemplified and described herein. In an embodiment the amount of microsponges may be varied from about 1% to about 25% of the formulation, preferably about 5% to 15%. Microsponge containing compositions are shown in Example 15. A person skilled in the art, will understand that the microsponge may be replaced by one or more other encapsomes in the compositions of the present invention.

In an embodiment any active agent suitable for loading in microsponges may be used, such as benzyl peroxide (BPO), tretinoin, hydroquinone, kotoprofen, vitamins, retinoids, such as retinoic acid isoretinoic acid and retinol, calcipotriol or calcitriol or tacalcitol (with or without a corticosteroid such as betmethasone or its esters (eg bmv)), flucinonide, hydrocortisone or clobetasol proprionate, flavanoids, fluconazole, ibuprofen, trolamine and the like. Where the active agent is oil soluble but not water soluble then formulations with minimal or no oil are preferred where the active agent is primarily to be located in the microsponges. So in an embodiment there is no oil in the formulations, only gels. In another embodiment, there are no significant amounts of true oils that solubilize the active ingredients and extract them from the microsponges. In an embodiment where the active ingredient is insoluble in water and is entrapped in the microsponges there is provided true oil in water emulsion, where the active ingredient is only exposed to the external water phase and does not access the internal oil phase. This may be achieved in an embodiment by formulating an aqueous oil gel foam with substantial water content. The methodology of loading microsponges with active agent and amounts that can be loaded are described in WO 01/85102, which is incorporated herein by way of reference. Where Drug Microsponge X % w/w is specified it refers to the microsponges including the trapped drug and any other ingredients incorporated when loading the microsponges.

"Dendrimers" are 3-dimensional polymeric materials of low polydispersity comprising repeatedly branched molecules, which are constructed by the successive addition of layers to the branching groups. Each new layer is called a generation. The final generation can incorporate additional active groups to tailor the functionality of the dendrimer. They can be neutral, anionic or cationic. The selection of core, branching and surface molecules gives the dendrimer the desired properties. Dendrimers are useful to prevent and to treat vaginal infections, sexually transmitted diseases, viral infections and HIV. They can be used against bacteria, yeast, fungi, or parasites.

Solubility of an Active Agent

In an embodiment, the active agent is not fully soluble in water or, is not fully soluble in the presence of a hydrophobic solvent in the formulation, or is not fully soluble in the oil phase of the emulsion. In an embodiment, the Poloxamer is present in the composition in an amount sufficient to solubilize the active agent in the composition. In one or more embodiments Poloxamer acts to improve the solubility of an active agent. In one or more embodiments Poloxamer enables the formulation to become clear. In a preferred embodiment the active agent to be solubilized is diclofenac or salicylic acid.

Exemplary Groups of Active Agents

NSAID

In an embodiment, the active agent is a non-steroidal anti-inflammatory agent. In the context, a nonsteroidal antiinflammatory agent (also termed herein "NSAID") is a pharmaceutically active compound, other than a corticosteroid, which affects the immune system in a fashion that results in a reduction, inhibition, prevention, amelioration or prevention of an inflammatory process and/or the symptoms of inflammation and or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is proinflammatory. Thus, in one or more embodiments, the NSAID is selected from the group consisting of a COX-1 inhibitor, a COX-2 inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof. In an embodiment, the Poloxamer is present in the composition in an amount sufficient to solubilize the NSAID, as exemplified herein by the solubilization of both diclofenac and salicylic acid in both non-emulsion and emulsion based compositions.

Steroids

In an embodiment, the active agent is a steroid. In certain embodiments the steroid is a corticosteroid, including but not limited to, hydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, as well as analogs, derivatives, salts, ions and complexes thereof.

In certain embodiments, the steroid is a hormone or a vitamin, as exemplified by pregnane, cholestane, ergostane, aldosterone, androsterone, calcidiol, calciol, calcitriol, calcipotriol, clomegestone, cholesterol, corticosterone, cortisol, cortisone, dihydrotestosterone, ergosterol, estradiol, estriol, estrone, ethinylestradiol, fusidic acid, lanosterol, prednisolone, prednisone, progesterone, spironolactone, timobesone and testosterone, as well as analogs, derivatives, salts, ions and complexes thereof.

In an embodiment, the Poloxamer is present in the composition in an amount sufficient to solubilize the steroid.

Immunomodulators

In an embodiment, the active agent is an immunomodulator. Immunomodulators are chemically or biologically-derived agents that modify the immune response or the functioning of the immune system. Immunomodulators suitable for use according to the present invention include, among other options, cyclic peptides, such as cyclosporine, tacrolimus, tresperimus, pimecrolimus, sirolimus (rapamycin), verolimus, laflunimus, laquinimod and imiquimod, as well as analogs, derivatives, salts, ions and complexes thereof. Such compounds, delivered in the foam, are especially advantageous in skin disorders such as psoriasis, eczema and atopic dermatitis, where the large skin areas are to be treated. In an embodiment, the Poloxamer is present in the composition in an amount sufficient to solubilize the immunomodulator.

Retinoids

In an embodiment, the active agent is a retinoid. The general formula of retinoids is:

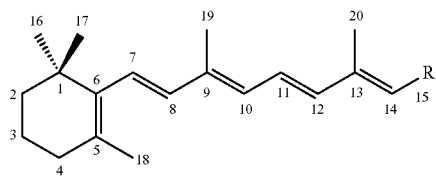

where R is selected from the group consisting of H, alkyl, aryl, alkenyl, benzyl, $CH_2OH$, $CH_2NH_2$, CHO, CH=NOH, $CO_2H$, CH=N$[CH_2]_4$CHNH$_2$CO$_2$H, $CH_3$, $CO_2C_2H_5$, $CH_2OCOCH_3$, a heteroatom, a saccharide and a polysaccharide.

Retinoids suitable for use according to the present invention include, among other options, include retinol, retinal, retinoic acid, isotretinoin, tazarotene, adapalene, 13-cis-retinoic acid, acitretin all-trans beta carotene, alpha carotene, lycopene, 9-cis-beta-carotene, lutein and zeaxanthin, as well as analogs, derivatives, salts, ions and complexes thereof.

Retinoids are known as sensitive agents, which tend to degrade in the presence of various formulation components, as well as oxygen, heat and light. Therefore, in certain embodiments, the retinoid is encapsulated in particles, microparticles, nanoparticles, microcapsules, microsphres, nanocapsules, nanospheres, liposomes, niosomes, polymer matrix, silica-gel, graphite, nanocrystals or microsponges. Such particles can have various functions, such as (1) protection of the retinoid from degradation; (2) modification of the retinoid release rate from the composition; (3) control of skin penetration profile; and (4) mitigation of adverse effects, due to the controlled release of the retinoid from the encapsulation particles.

Antiinfective Agents

In an embodiment, the active agent is an antiinfective agent. Such anti-infective agent can be selected from the group of an antibiotic agent, an antibacterial agent, an antifungal agent, an agent that controls yeast, an antiviral agent and an antiparasitic agent. Exemplary antiinfective agents are exemplified by beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions and complexes thereof.

Cells as Active Agents

In an embodiment, the active agent is a therapeutic cell, or a mixture of therapeutic cells, or culture of therapeutic cells. In another embodiment the active agent is a fragment or fraction of a therapeutic cell, a mixture of therapeutic cells, or culture of therapeutic cells. In a further embodiment a fragment or fraction of the therapeutic cells can be one or more of cell organelles, such as mitochondria, golgi apparatus, endoplasmic reticulum, lysosomes, nucleus, cell membrane, and the like. The therapeutic cells, as provided in the present invention are cells that have a therapeutic benefit, through a variety of mechanisms, treatment modes and pathways. Without claiming specific mechanisms of action, the therapeutic cells, or fragments or fractions thereof can have an effect on microbial, bacteria, fungal or viral infection, autoimmune conditions, tumors, metastases, wound, burn, ulcer and post operative injury. The therapeutic cells can act directly on the condition, or via releasing signaling agents, such as cytokines, chemokines and the like. In one or more embodiments, therapeutic cells, fragments and fractions can include stem cells, blood cells, nerve cells or other cells of human origin. In an embodiment the cells produce antisense therapy. In a particular embodiment the therapeutic cells can be engineered to provide gene therapy. Genes are inserted into an individual's cells to treat a disease including hereditary diseases. The cells are then administered to the individual. The gene therapy may be somatic or it may be germ line gene therapy. In another embodiment the therapeutic cells may act to bolster or stimulate the subject's immune system. In an embodiment, the cells are selected from the group consisting of fibroblasts, langerhans cells, keratinocytes, leukocytes, phagocytes (such as macrophages, neutrophils, and dendritic cells), mast cells, eosinophils, basophils, and natural killer cells. In other embodiments, the cells are skin cells, such as fibroblasts, langerhans cells and keratinocytes. Such cells may in one or more embodiments be in the early sages of development or differentiation. In one or more embodiments the cells may be inverted, for example, ghost cells. In other embodiments the cells are of plant, bacterial or viral origin and can include phages. In one or more embodiments the cells secrete an active agent such as a hormone or a neuro-transmitter or a cytokine or a chemokine or an interferon and the like. Cytokines have been variously named as lymphokines, interleukins, and chemokines. Cytokines are a category of signaling proteins and glycoproteins that, are used extensively in cellular communication. Cytokines are a diverse class of compounds in terms of origin and purpose. They are produced by a wide variety of hematopoietic and non-hematopoietic cell types and can have effects on both nearby cells or throughout the organism, sometimes strongly dependent on the presence of other chemicals. The cytokine family consists mainly of smaller, water-soluble proteins and glycoproteins with a mass of between 8 and 30 kDa. Chemokines can guide the migration of cells. Cells that are attracted by chemokines follow a signal of increasing chemokine concentration towards the source of the chemokine. Their activities include directing lymphocytes; promoting angiogenesis; guide cells to tissues that provide specific signals critical for cellular maturation; inflammatory in response to bacterial infection, viruses and agents that cause physical damage. Their release is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. They are released by many different cell types and serve to guide cells of both innate immune system and adaptive immune system. In an embodiment cells which secrete one or more of the following classes of cytokines is selected: CC cytokines; CXC cytokines; C cytokines; CX3C cytokines.

In an embodiment, the therapeutic cells are included in the composition in a concentration, suitable for an effective treatment of a disease or condition. Mixtures of different therapeutic cells are contemplated.

An exemplary composition which is suitable as a cell therapy composition includes:
  a. an aqueous solution, suitable to maintain therapeutic cells in viable state;
  b. a Poloxamer/polymer system, selected from the group of:
    i. about 20% a Poloxamer; and
    ii. a combination of (1) up to about 5% a Poloxamer; and (2) a polymeric agent, wherein the polymeric agent is added in an amount which, by itself, is not sufficient to produce a gel; and
  c. therapeutic cells.

A further exemplary composition which is suitable as a cell therapy composition includes:
  a) an aqueous solution, suitable to maintain therapeutic cell fractions or fragments or mixtures of therapeutic cells and therapeutic cell fractions or fragments in a viable state;
  b) a Poloxamer/polymer system, selected from the group of:
    i. about 20% of a Poloxamer; and
    ii. a combination of (1) up to about 5% of a Poloxamer; and (2) a polymeric agent, wherein the polymeric agent is added in an amount which, by itself, is not sufficient to produce a gel; and
  c) therapeutic cell fractions or fragments alone or in combination with therapeutic cells.

In an embodiment, the Poloxamer/polymer system is included in the composition in a concentration which suitable to keep the cells in viable state. In an embodiment, the Poloxamer is included in the composition in a concentration which enhances the therapeutic effect of the therapeutic cells.

In a preferred embodiment the Poloxamer is a fixing Poloxamer. In a more preferred embodiment the fixing Poloxamer is Poloxamer 407.

In an embodiment, the Poloxamer/polymer system is included in the composition in a concentration or concentration ratio that, at low temperature, such as about 20° C. or lower, the composition is flowable, while upon application to a body surface, having temperature of more than about 30° C., it creates a more viscous composition. This can be achieved by selecting an effective amount of a suitable fixing Poloxamer.

In an embodiment the more viscous composition is semi-fluid. In a preferred embodiment the composition becomes a substantially non-flowable gel. This property is particularly important, in the event that it is desirable to deliver the composition, containing therapeutic cells to a target site as a liquid, but to fix it at the target site upon application or to improve the retention time. If the composition is to be delivered as a liquid to a body cavity it can be advantageous that it becomes a gel upon exposure to body temperature since this will facilitate or improve its retention in the body cavity. Likewise, if the composition is to be delivered as a foam, then upon application to a target site as the foams temperature increases its collapse time will increase and after the foam is broken by gentle mechanical force it may have gel or semi gel like properties so it conveniently remains at the target site. If the foam is applied to a body cavity then as indicated above upon exposure to body temperature this property will facilitate or improve its retention in the body cavity. In an unexpected discovery it has been found that fixing may occur at low concentrations of fixing Poloxamer synergistically in combination with a polysacharide.

Exemplary concentrations of a Poloxamer alone are about 20% or more, in the case of Poloxamer 407.

It was surprisingly discovered that while concentrations of less than about 20% of a Poloxamer, are not sufficient to produce a non-flowable gel upon application to a body surface, having temperature of more than about 30° C., a combination of a Poloxamer and a polymer affords synergistically a non-flowable gel upon application to a body surface, having temperature of more than about 30° C. at much lower concentrations. Exemplary concentrations of Poloxamer/polymer combination system is about 1% or more of Poloxamer 407 and about 0.5% or more or about 0.7% or more of a polymeric agent.

Exemplary suitable polymers include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid (which can also be obtained from biotechnological processes); chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene, such as Carbopol® 934, Carbopol® 940, Carbopol® 941, Carbopol® 980 and Carbopol® 981. Polyethylene glycol, having molecular weight of 1000 or more (e.g., PEG 1,000, PEG 4,000, PEG 6,000 and PEG 10,000) also have gelling capacity and while they are also considered herein as "polar solvents", they are also considered polymeric agents. Mixtures of polymeric agents are contemplated.

In a preferred embodiment the polymer is a polysacharide, In a more preferred embodiment the polysachharide is a cell derived polysachharide like xantham gum or hyaluronic acid.

In an embodiment, the Poloxamer/polymer system is included in the composition in an optimized concentration or concentration ratio that, in one aspect, at low temperature, such as about 20° C. or lower, the composition is flowable, while upon application to a body surface, having temperature of more than about 30° C., it creates a non-flowable gel, and in an additional aspect, it is suitable to keep the cells in viable state.

In an embodiment, the composition provides a synergistic effect, resulting from the direct activity of the therapeutic cells, and the induction of release of signaling agents, such as cytokines, chemokines and the like, either from the therapeutic cells or from other cells present in the viable tissue of the target site.

In an embodiment, the composition, comprising a Poloxamer or a Poloxamer/polymer system and therapeutic cells, as described above, is packaged in an aerosol container, equipped with a valve and an actuator, capable of releasing a foam and pressurized with a liquefied or compressed propellant at a concentration of about 1% to about 25% by weight of the total composition.

Dual Chamber

Dual and Multi Chamber devices and heads suitable for use with the formulations described herein where a first formulation is stored in a first canister and a second formulation is stored in a second canister are described in U.S. Pat. No. 6,305,578 entitled DEVICE FOR MIXING, FOAMING AND DISPENSING LIQUIDS FROM SEPARATE COMPRESSED-GAS CONTAINERS and in US Publication 2007-0069046 and entitled APPARATUS AND METHOD FOR RELEASING A MEASURE OF CONTENT FROM A PLURALITY OF CONTAINERS all of which are incorporated herein by reference in their entirety. More particularly any of the devices and uses described are applicable herein and are incorporated by reference.

In an embodiment the dual chamber device is as described in U.S. Pat. No. 6,305,578 for example, a compressed gas container apparatus, having at least two compressed gas containers, disposed side by side, each for one foamable liquid product which contains a liquefied propellant gas, wherein both compressed gas containers are each provided with a valve, both valves are actuatable in common by a top fitting, and each valve is provided through the top fitting with a connecting conduit, the connecting conduits discharge into a mixing chamber, and an expansion conduit adjoins the mixing chamber and on its end has a foam dispensing opening, characterized in that the connecting conduits and the mixing chamber have such small cross-sectional areas that when a product is dispensed, the products flowing through the connecting conduits) and the mixing chamber remain in a liquid phase.

In an embodiment the dual dispenser head is as described in US Publication 2007-0069046 for example:

a dispenser head for use with a plurality of containers, comprising:
 (a) an actuator, wherein the dispensing head is structured and positioned to be an actuator or comprises an actuator button disposed within the dispensing head to simultaneously actuate the plurality of containers
 (b) a flow guide comprising
  (A) a plurality of flow conduits disposed within the flow guide; and
  (B) for each of the plurality of flow conduits,
   (i) an inlet through a wall of the flow guide connecting with a flow conduit; and
   (ii) an outlet from a flow conduit through a wall of the flow guide;
  (C) and for each of the plurality of inlets and containers, a linker, each to link an inlet and a container to allow the contents of the container upon actuation to pass through the inlet and through the flow conduit to reach and pass through the outlet;
  (D) and wherein the flow guide is structured and positioned to allow simultaneous flow communication between each of the plurality of flow conduits and wherein the plurality of outlets are structured and positioned to allow substantially contemporaneously dispensing and/or combining of the content from a plurality of containers external to the dispensing head.

In one or more embodiments the dual canister kit may include a bag in canister or bag on valve system for one or both of the compositions.

In one or more embodiments the dual chamber system is adapted and arranged to provide mixing of the contents of the canisters in a mixing means connected to the canisters.

In one or more embodiments the dual chamber system is adapted and arranged to provide uniform dosing of the contents of each canister by a metered dosing means connected to the canisters.

In one or more embodiments there is provided a kit comprising a dual chamber device or dual dispenser head, a first canister comprising a first foamable formulation comprising a first API and a second canister comprising a second foamable formulation comprising a second API wherein each canister is connectable to the said device or head. The first foamable formulation may be any of the Poloxamer formulations described herein and the second foamable formulation may also be any of the Poloxamer formulations described herein. In an embodiment the first API is a steroid and the second API is a vitamin D derivative and the each formulation is adapted to carry an effective amount of steroid and vitamin D derivative, respectively, such that each formulation and API is sufficiently chemically and physically stable for pharmaceutical use.

In another embodiment the second foamable formulation is one of the therapeutic cell foamable compositions described Example 16 below. In another embodiment as indicated under example 16 the first formulation is a Poloxamer formulation and the second formulation is an aqueous formulation comprising therapeutic cells or cell fragments/fractions or mixtures thereof. Similarly In another embodiment the second foamable formulation can be one of the microsponge foamable compositions described Example 15 below.

Fields of Applications

The foamable composition is suitable for the treatment of any inflicted surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site"). In the context herein "treatment" can mean any administration or application of a remedy to a patient that is intended to prevent, cure or decrease the symptoms of a disease or disorder, or to relieve pain, anxiety or any form of perceived discomfort.

By selecting a suitable active agent, or a combination of two or more active agents, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the disorder is a dermatological disorder, which can be treated by a Poloxamer.

In an embodiment, the disorder is a dermatological disorder, which can be synergistically treated by an active agent, together with a Poloxamer.

In an embodiment, the disorder is a dermatological disorder, which can be treated by a topical steroid.

In an embodiment, the disorder is a dermatological disorder, which can be treated by an immunomodulator.

In an embodiment, the disorder is a dermatological disorder, which can be treated by a retinoid.

In an embodiment, the disorder is a dermatological disorder, which can be treated by cell therapy.

In an embodiment, the disorder is a dermatological disorder, which can be treated by gene therapy.

In an embodiment, the disorder is a dermatological disorder, which can be treated by cytochine.

In an embodiment, the disorder is a dermatological disorder, which can be treated by chemotherapy.

In an embodiment, the disorder is a dermatological disorder, which can be treated by an anti-infective agent, such as an antibacterial agent, and antibiotic, an antifungal agent and an antiviral agent.

In an embodiment, the disorder is a dermatological disorder, which is common in children. Foam is advantageous in the topical treatment of children, who are sensitive to treatment with a cream or ointment.

In an embodiment, the disorder is atopic dermatitis and the active agent is a steroid, a NSAID or an immunomodulator.

In an embodiment, the disorder is psoriasis and the active agent is a steroid, a NSAID, a retinoid or an immunomodulator.

In an embodiment, the disorder is selected from psoriasis and atopic dermatitis and the active agent comprises a steroid, together with an additional non-steroidal active agent, such as a vitamin D derivative.

In an embodiment, the active agent a NSAID, and the disorder is selected from the group consisting of acne, rosacea, actinic keratoses, joint pain, back pain, superficial pain and the like and osteoarthritis.

In an embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment, the composition is useful for the treatment of wound, ulcer and burn.

The composition is also suitable for administering a hormone to the skin or to a mucosal membrane or to a body cavity, in order to deliver the hormone into the tissue of the target organ, in any disorder that responds to treatment with a hormone.

In an embodiment, the Poloxamer composition can be applied to protect the skin prior to exposure to radiation or to help or accelerate the healing after exposure to radiation. In a preferred embodiment the polymer in the Poloxamer/polymer aqueous composition is hyaluronic acid.

Canisters

Each aerosol canister is filled with the pre-foam formulation ("PFF") and crimped with valve using vacuum crimping machine and then pressurized with propellant. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing is carried out using a hydrocarbon gas or gas mixture. Canisters are filled and then warmed for 30 sec in a warm bath at 50° C. and well shaken immediately thereafter.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

In an embodiment, where there are therapeutic cells the propellant is separate from the therapeutic cells Poloxamer formulation and the product is assembled using a bag on valve system or bag in can canister assembly in which the product is in a sealed bag inside the sealed canister which has been filled with propellant. Upon actuation the propellant exerts pressure on the bag to expel its contents. In a further embodiment the propellant mixes with the product as it is being released from the canister. In another embodiment a dual canister assembly is used wherein the therapeutic cells are in bag in can or bag in valve system and the Poloxamer formulation is in a second canister and they are mixed either externally or in a mixing chamber connected to both canisters as is known in the art and or as described above. Where therapeutic cells are used the propellant will be selected such that an effective amount of therapeutic cells will be available after expulsion from the canister/bag in valve. Suitable propellants include compressed air, $CO_2$ nitrogen, helium, argon, or nitrous oxide.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Tests to Characterize Foam Products

By way of non limiting example the objectives of hardness, collapse time, FTC stability tests and aging are briefly set out below as would be appreciated by a person skilled in the art.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 minute. Thus foams which are structurally stable on the skin for at least one minute are termed "short term stable" compositions or foams.

Drainage: A simple indication of the rate of drainage or whether there is any significant drainage can be obtained from the collapse time method and results. In the collapse time method the foam is observed and filmed for a period of time, say 180 secs. The height of the foam is measured against a marked ruler and any changes recorded and plotted as a graph. Also the foam quality is observed. If during the measurement there is a change in quality it is noted. So simply if there is a reduction in quality say from Good to Fairly Good or from Excellent to Good then significant drainage is considered to have occurred and the approximate time point when this change has been noted is said to be the drainage time. A slow drainage is a drainage of about or more than 180 secs preferably more than 300 seconds.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a preweighed tube, filling it until excess is extruded. Immediately remove (level off) excess foam at both ends and then weigh the filled tube on the weighing balance.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude. Unless otherwise stated viscosity of the pre-foam formulation (PFF) is provided. It is not practical to try and measure the viscosity of the foamable formulation with regular propellants since they have to be stored in sealed pressurized canisters or bottles. In order to simulate the viscosity in the foamable formulations with propellant an equivalent weight of pentane (a low volatile hydrocarbon) is added to and mixed with the pre-foam formulation and left overnight. The viscosity is then measured as above.

Freeze Thaw Cycles (FTC)

To check the foam appearance under extreme conditions of repeated cycles of cooling, heating (first cycle) cooling, heating (second cycle) etc., commencing with -10° C. (24 hours) followed by +40° C. (24 hours) measuring the appearance and again repeating the cycle for up to three times.

Sensation

Healthy volunteers selected at random were give a sample of foam formulation and applied it to the skin on their hand or forearm and were asked for their observations.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

The light microscope enables observing and measuring particles from few millimeters down to one micron. Light microscope is limited by the visible light wavelength and therefore is useful to measuring size of particles above 800 nanometers and practically from 1 micron (1,000 nanometers).

Shakability

"Shakability" represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non shakable. This property may be of particular importance in cases where shaking is required for affecting proper dispersion of the contents.

Shakability Scoring:

| | |
|---|---|
| Good shakability (conforms to required quality specification) | 2 |
| Moderate shakability (conforms to required quality specification) | 1 |
| Not or hardly shakable but may still be flowable and allow foam formation of quality | 0 |
| Is substantially not able to pass through valve | Block |

Aging or Creaming by Centrifugation:

1. Principle of Test

The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion.

In the case of waterless silicone emulsion compositions which are inherently more susceptible to creaming by virtue of the silicone and by virtue of the waterless solvent, the presence of some creaming at the enormous centrifugal forces imposed on the formulations does not derogate from the fact that the compositions have not phase separated and can still be understood as being resistant to creaming and provides a good indication of the long term stability of the formulations. To the extent that good quality stable formulations are achieved, which are resistant to creaming or such that no creaming is observed, the formulations are considered as exceptionally stable. The procedure is as follows:

1. Following preparation of the experimental formulation/s, allow to stand at room temperature for ≥24 h.
2. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.
3. Transfer each mixture to 1.5 mL microtubes. Tap each microtube on the table surface to remove entrapped air bubbles.
4. Place visually balanced microtubes in the centrifuge rotor and operate the centrifuge at about 300 rpm for 10 min. about 1,000 rpm for 10 min. or at about 3,000 rpm for 10 min or at about 10,000 rpm for 10 min. The centrifuge can be a BHG HEMLE Z 231 M.
5. Centrifugation can also be executed at a higher rpm for a shorter period or a lower rpm for a longer period bearing in mind the G force experienced by the formulations is many fold greater than the one G to which a formulation would be exposed to during its shelf life.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at one or more of 5 C, at 25 C, at, 40 C and at 50 C. At appropriate time intervals canisters are removed and the amount of active agent in the foam sample is measured.

EXAMPLES

The invention is described with reference to the following examples. This invention is not limited to these examples and experiments. Many variations will suggest themselves and are within the full intended scope of the appended claims.

The ingredients listed in the Examples are Xanthan, Poloxamer 188, Poloxmar 124, Poloxamer 407, Pemulen TR2, Carbomer 974 Methocel, PVP, NaCMC, PEG 100 stearate, Laureth 23, Polysorbate 60, Polysorbate 80, Sorbitan oleate, Sorbitan laurate, Cyclomethicone, Dimethicone, Dimethicone cyclomethicone copolyol, Glycerin, Propylene glycol, Heavy mineral oil, Salycilic acid, Clindomycin, Acyclovir, Minoxid, Benzoyl peroxide, Sodium diclofenac.

A. CARRIER EXAMPLES

Section A

Example 1

Comparison of Different Polymeric Agents at Low Concentrations in Water with Propellant Part A—Xantham at 0.3% by Weight

| Ingredients | 011 w/w |
|---|---|
| Xanthan gum | 0.30 |
| Purified Water | to 100 |
| Propellant AP-70 % | 8.00 |
| Viscosity | 637.86 |
| Viscosity (+8% pentane) | 685.85 |
| Foam Quality | Fair* |
| Density | 0.279 |
| Bubble size | 126 |
| Bubble size (above 500 μm) | 0.0 |

*aerated gel

Procedure: Xanthan was dissolved in water and mixed until fully dissolved at room temperature.

Comments: xanthan a polysaccharide is only able to produce a bubbled semi liquid gel of high density.

Part B—Polymeric Agents at 5% in Water with Propellant Foam Vehicle Composition, Containing Poloxamer 188

| Ingredient | 5% Poloxamer (188) |
|---|---|
| Poloxamer 188 | 5.00 |
| Purified water | 95.00 |
| Total | 100.00 |
| Propellant (AP-70) | 8.00 |

Foam Properties

| | |
|---|---|
| Foam quality | Good |
| Color | white |
| Odor | no odor |
| Density (g/mL) | <0.1 |
| Cooling Sensation on Hand | Yes |

Procedure: Poloxamer 188 was dissolved in water and mixed until fully dissolved at room temperature Comments: Unexpectedly, 5% Poloxamer 188, with no further ingredients, is sufficient to produce good foam at room temperature with high expansion (density of less that 0.1 g/mL), easily spreadable and quick absorption into the skin upon application.

Part C—Polymeric Agents at Different %s in Water with Propellant

Foam Vehicle Composition Containing 1% to 15% Poloxamer 407

| Ingredient | 1% W/W 01 | 2% W/W 015 | 3% W/W016 | 4% W/W 017 | 5% W/W 018 | 15% W/W X |
|---|---|---|---|---|---|---|
| Poloxamer 407 (20% solution) | | 10.00 | 15.00 | 20.00 | 25.00 | 75.00 |
| Poloxamer 407 (powder) | 1.00 | | | | | |
| Purified water | 99.00 | 90.00 | 85.00 | 80.00 | 75.00 | 25.00 |
| Total | 100.00 | 100.00 | 100.00 | 100.00 | 100.00 | 100.00 |
| Propellant A70 | 8.00 | 8.00 | 8.00 | 8.00 | 8.00 | 8.00 |
| PFF | 01 | 015 | 016 | 017 | 018 | X |
| Viscosity | 7.00 | 0.00 | 0.00 | 0.00 | 0.00 | NM |
| Viscosity (+8% pentane) | NM | 0.00 | 0.00 | 0.00 | 0.00 | NM |
| pH | 6.78 | NM | NM | NM | NM | NM |
| Foam | | | | | | |
| Foam Quality | Fairly good | Good | Excellent | Excellent | Excellent | Excellent |
| Odor | No odor | No odor | No odor | No odor | No odor | No odor |
| color | white | white | white | color | white | white |
| Shakability of PF after propellant addition. | None | None | None | None | None | NM |
| pH | 6.34 | NM | NM | NM | NM | NM |
| Density | NM | 0.067 | 0.063 | 0.081 | 0.054 | <0.1 |
| Collapse time | NM | 180/FG | 140/FG | >180/FG | 120/F | NM |
| Drainage Time | NM | 120 | 120 | 120 | 30 | NM |
| Bubble size | 93 | 144 | 159 | 117 | 140 | NM |
| Visual inspection in glass bottle | NM | NM | NM | NM | Non homogenous | NM |
| Total dispense weight | | 100.3 | 91.6 | 95.7 | 98.7 | NM |

NM = Not measured.

Procedure: A stock solution of 20% Poloxamer was prepared by dissolving the poloxamer in water at 5° C. overnight until fully dissolved. 1% Poloxamer was prepared by dissolving 1 g solid Poloxamer in water at room temperature. Higher levels of Poloxamer (about 2% and above) do not dissolve readily and therefore require the preparation of a stock solution overnight with cooling. Poloxamer stock solution was mixed with water at room temperature.

Comments: Interestingly, it was observed that formulations were of enhanced quality when they were prepared using stock Poloxamer solution instead of adding Poloxamer powder directly. In high concentrations, difficulty was encountered in dissolving Poloxamer 407 in water. Therefore the use of stock solution was employed. Viscosity of PFF was seen to be about zero due to the very high aqueous content.

The quality of the foam was seen to be concentration dependant and improved with increased concentration. The fact foam was produced was unexpected due to the following reasons. First the formulation is of hydrophilic nature and the hydrophobic propellant is likely not to dissolve in the aqueous solution. This may be explained by the fact that Poloxamer is comprised of a polyoxyethylene segment which is hydrophilic while the polyoxypropylene segment is hydrophobic. Secondly there is no foam booster present such as surfactant. Poloxamers overall are known to be used as mild emulsifiers. In one case when the formulation was made in a pressurized glass bottle it appeared to be non homogenous yet surprisingly the foam quality was excellent and dispense weight satisfactory. More particularly, the foamable carrier demonstrated good quality foam when above 2% Poloxamer was used. When 1% was dissolved in water, foam quality was determined as fairly good (FG). Total dispense weight was high. The 3% poloxamer foam demonstrated total lower dispense weight (91%) in comparison to other formulations. Bubble size was somewhat higher than expected with excellent quality foam formulations and the dispensing rate was not always homogenous. All foams reduced from high quality to low (FG) when collapse time was evaluated. About 3% to about 4% Poloxamer foam appeared to provide the best foam quality. Using stock solution improved foam quality since solubility was improved. Due to the gelling characteristics of Poloxamer formulations shakability was minimal to none and yet viscosity was low due to large quantity of water. This may be explained by the expansion ability of the polymer.

It appears that the propellant is not fully dissolved in the foam due to the hydrophobic nature of the propellant. This was demonstrated by visual inspection of pentane addition to the pre foam formulation (PFF). Pentane can simulate the effect of volatile propellant. Interestingly although the propellant was not dissolved in the formulation, the dispense weight was high, indicating the propellant was able to dispense the formulation from the canister.

Section B

Carbopol and Poloxamer

Procedure: Carpobol 974 was mixed vigorously with water at room temperature until fully dissolved followed by the addition of trolamine to reach the required pH. Poloxamer 407 stock solution was added to the carbopol solution and mixed at room temperature.

Example 2A pH Effect of Poloxamer with Carbopol

|  | 01 | 02 | 03 | 04 | 05 |
|---|---|---|---|---|---|
| Ingredient |  |  |  |  |  |
| Carbopol 974 | 0.30 | 0.30 | 0.30 | 0.30 | 0.30 |
| trolamine | ~pH~3 | to pH ~4 | to pH ~5 | to pH ~6 | to pH ~7 |
| Poloxamer 407 | 2.00 | 2.00 | 2.00 | 2.00 | 2.00 |
| Purified Water | to 100 | to 100 | to 100 | to 100 | to 100 |
| pH final |  |  |  |  |  |
| Propellant AP70 | 8.00 | 8.00 | 8.00 | 8.00 | 8.00 |
| PFF |  |  |  |  |  |
| Viscosity | 2.00 | 1377.71 | 8926.1 | 14988.80 | 16076.57 |
| Viscosity (+8% pentane) | 14.00 | 1614.66 | 10029.86 | 153214.73 | 14652.00 |
| pH | NM | NM | NM | NM | NM |
| Foam |  |  |  |  |  |
| Foam Quality | good | excellent | excellent | excellent | excellent |
| Odor | No odor | No odor | No odor | No odor | No odor |
| Shakability of PF after propellant addition | moderate | moderate | moderate | moderate | moderate |
| pH | 4.07 | 4.92 | 5.41 | 6.53 | 7.32 |
| Density | 0.089 | 0.091 | 0.105 | 0.124 | 0.318 |
| Collapse time | >180/G | >180/G | >180/G | >180/E | >180/E |
| Drainage Time | >180 | 60 | 180 | >180 | >180 |
| Bubble size | 142 | 123 | 146 | 121 | 141 |
| Total dispense weight | NM | 92.96 | NM | NM | 86.33 |

*estimated

Comments: Carbopol in combination with Poloxamer produced excellent foam with long collapse and drainage times. Viscosity and density were increased as pH was elevated. At each pH the viscosity was not significantly different in the presence or absence of pentane, suggesting better solubility of the propellant in the formulation. When the formulations were mixed with pentane large bubbles trapping the pentane were observed.

Foam demonstrated high stability and shakability was improved. Bubble size was similar for all formulations. However, total dispense weight was reduced when tested for formulations 02 and 05 suggesting in these two cases lesser homogeneity with the propellant.

Example 2B

Poloxamer with Carbopol-pH Studies

Effect of Halving the Carbopol Concentration

Carboxamer/Poloxamer Concentration in Foamable Polymer Compositions

| Ingredient | 090A % w/w | 090B % w/w | 090C % w/w | 090D % w/w |
|---|---|---|---|---|
| Water, purified | 96.80 | 97.40 | 97.00 | 97.50 |
| Carbomer 974P, NF | 0.80 | 0.40 | 0.80 | 0.40 |
| Trolamine | 0.40 | 0.20 | 0.20 | 0.10 |
| Poloxamer 407 | 2.00 | 2.00 | 2.00 | 2.00 |
| Total | 100.00 | 100.00 | 100.00 | 100.00 |

-continued

| Ingredient | 090A % w/w | 090B % w/w | 090C % w/w | 090D % w/w |
|---|---|---|---|---|
| Propellant AP-70 % | 8.00 | 8.00 | 8.00 | 8-00 |
| Foam quality | Good | Good | Good | Good |
| Foam density | 0.114 | 0.067 | 0.092 | 0.064 |
| Shakability of PF after propellant addition | Good | Good | Good | Good |

Comments: A combination of Carbomer with Poloxamer provides the preparation of shakable foamable compositions with 96-98% water, with good foam quality. The density of these compositions is low and ranges from 0.06-0.12 g/cm$^3$. It is thought that there is some form of synergism between Poloxamer and carbomer such that the combination provides enhanced foam quality.

Section C

Pemulen and Poloxamer

Procedure: Carbopol is dissolved in water followed by the addition of trolamine and at room temperature. When a gel is formed, Poloxamer is slowly added to the mixture.

Example 3

Foamable Compositions Comprising Pemulen with or without Poloxamer

| Ingredient | 086 | 087 |
|---|---|---|
| Pemulen TR2 | 0.50 | 0.50 |
| Trolamine | 0.50 | 0.50 |
| Poloxamer 407 |  | 2.00 |
| Poloxamer 188 | 5.00 |  |
| Water, purified | 94.00 | 97.00 |
| Total | 100.00 | 100.00 |
| Propellant AP-70 % | 8.00 | 8.00 |
| PFF |  |  |
| Centrifugation 3000 rpm/10 min | NM | NM |
| Centrifugation 10000 rpm/10 min | NM | NM |
| Viscosity, cP | NM | NM |
| Foam |  |  |
| Foam quality | Excellent | Excellent |
| Foam density, g/mL | 0.046 | 0.058 |
| Hardness, g | NM | NM |
| Collapse time, sec | NM | NM |
| Foam drainage, sec | NM | NM |
| Shakability of PF after propellant addition | Good | Good |
| pH | NM | NM |
| pH diluted 1:5 | NM | NM |
| Mean bubble size mcm | NM | NM |
| Drainage time approx. [min] | NM | NM |

Comments: Interestingly, a combination of pemulen and 2%-5% of a Poloxamer compound, resulted in a foam composition of excellent quality, exhibiting a density of 0.04-0.06 g/cm$^3$ It is thought that there is some form of synergism between the Poloxamer and the pemulen to enhance the foam quality and stability. It may be—without being bound by any theory—that solubility of the propellant is enhanced in the presence of pemulen. The presence of trolamine increases the pH, causing the uncoiling and expansion of the polymers, assisting with a synergistic effect of those reagents.

Section D

Methocel or NaCMC or PVP and Poloxamer

Example 4

Foam Vehicle Composition, Containing Poloxamer 407 and a Polymer

| Ingredient | 07 | 08 | XXXX |
|---|---|---|---|
| Poloxamer 407 % W/W | 1.00 | 1.00 | 1.00 |
| Poloxamer 407 (20% solution) | 5.00 | 5.00 | 5.00 |
| Methocel | 0.5 |  |  |
| PVP |  | 0.5 |  |
| NaCMC |  |  | 0.50 |
| Purified water | 94.50 | 94.50 | 94.50 |
| Total | 100.00 | 100.00 | 100.00 |
| Propellant A70 | 8.00 | 8.00 | 8.00 |

| | 07 | 08 | XXXX |
|---|---|---|---|
| PFF |  |  |  |
| Viscosity | 115.98 | 0.00 | NM |
| Viscosity (+8% pentane) | 135.97 | 0.00 | NM |
| pH | 6.69 |  | NM |
| Foam |  |  |  |
| Foam Quality | Excellent | Good | Excellent |
| Odor | No odor | No odor | No odor |
| pH | 6.44 | NM | NM |
| Density | 0.07 | 0.056 | <0.1 |
| Collapse time | >180/G | 90/F | >300/FG |
| Drainage Time | 150 | 90 | NM |
| Bubble size | 132 | 173 | NM |
| Total dispense weight | 97.44 | 96.6 | NM |

Procedure: Methocel was dissolved in cold water 5° C. with mixing. PVP and NaCMC were dissolved at room temperature. Poloxamer 407 was added to the mixture until fully dissolved.

Comments: 1% Poloxamer failed to produce foam of quality therefore addition of polymers such as PVP and cellulose was tested. Methocel and CMC which are cellulose polymers produced foam of high quality which was stable over 3 mins, demonstrating the synergistic effect. PVP in comparison produced foam, which demonstrated lower stability.

Note: When the foam using CMC was dispensed on an inert dish at room temperature the resultant foam was of good quality. When the foam was applied to the hand, foam quality became fairly good.

Section E

Xantham and Poloxamer

Example 5

Poloxamer/Polymer Vehicle Gel Compositions were Examined without Propellant

Poloxamer/water compositions were tested in order to assess the behavior of Poloxamer formulations in the absence of propellant with and without a non surfactant polymer such as xanthan gum.

Procedure: 20% poloxamer stock solution was mixed with water at room temperature.

a) Poloxamer alone is a fluid below 20%

| | 20% | 15% |
|---|---|---|
| Poloxamer 407 | | |
| Water | To 100% | To 100% |
| Behavior on hand (PFF at RT) | Gel | Fluid |
| Behavior on hand (PFF at 36° C.) | Gel | Fluid |
| Behavior on glass at 36° C. (PFF at RT) | Gel | Fluid |
| Behavior on glass at 36° C. (PFF at 36° C.) | Gel | Fluid | b) Poloxamer 407 and polysaccharide xantham gum

| Poloxamer 407 | 15% | 15% | 10% | 5% | 2.5% | 1.0% |
|---|---|---|---|---|---|---|
| Xanthan gum | 0.12% | 0.5% | 0.5% | 0.5% | 0.7% | 0.7% |
| Water | To 100% | To 100% | To 100% | To 100% | To 100% | To 100% |
| Behavior on hand (PFF at RT) | Fluid | Gel | Gel | Gel | Gel | Gel |
| Behavior on glass at 36° C. (PFF at RT) | Fluid | Semi-Fluid | Fluid | Fluid | Semi-Fluid | Semi-Fluid |
| Behavior on hand (PFF at 36° C.) | Fluid | Semi-Fluid | Fluid | Fluid | Semi-Fluid | Semi-Fluid |
| Behavior on glass at 36° C. (PFF at 36° C.) | Fluid | Semi-Fluid | Fluid | Fluid | Semi-Fluid | Semi-Fluid | c) Poloxamer 188 and a non surfactant polysaccharide xantham gum

| Poloxamer 188 | 5% | 1.0% |
|---|---|---|
| Xanthan gum | 0.5% | 0.7% |
| Water | To 100% | To 100% |
| Behavior on hand (PFF at RT) | Gel | Gel |
| Behavior on glass at 36 C. (PFF at RT) | Gel | Gel | d) A non surfactant polysaccharide xantham gum alone

| Xanthan gum | 0.5% | 0.7% | 2.0% |
|---|---|---|---|
| Water | To 100% | To 100% | To 100% |
| Behavior on hand (PFF at RT) | Fluid | Fluid | Gel |

It was observed when 20% Poloxamer 407 PFF is at a relatively low temperature, such as about 20° C. or lower, the viscosity is lower and the composition is flowable, As the temperature increases to that of body temperature the viscosity increases such that upon application to a body surface, having temperature of more than about 30° C., it creates a non-flowable gel.

The above compositions were placed in transparent vials and were observed to be liquid at 20° C. Each one of the compositions was subsequently dripped on the palm of the hand (having temperature of about 32-35° C.; and the flowability was assessed by visual observation.

At 20% Poloxamer 407 alone the formulation was a gel at room and at body temperature. When the concentration of Poloxamer alone was reduced to 15% it became fluid.

It was found that the addition of a small amount of non surfactant polymer (xanthan gum) can act synergistically with 5% or 2.5% or 1% Poloxamer 407 a surfactant like polymer in order to achieve the gel like properties seen at 20% Poloxamer concentration alone, Poloxamer 188 (5%), in contrast 407, did not show a change in state and remained a gel when contacted with a surface at 36 C. Thus, the body temperature sensitive rheology of 407 is not observed with 188.

Xantham on its own remains fluid at concentrations at which it is a gel when combined with Poloxamer. Much higher amounts of xanthan gum are required to form a gel without Poloxamer.

These vehicles are suitable as carriers of various active agents, including therapeutic cells. These vehicles are suitable for application onto any body surface, including for example the skin, any body cavity and any mucosal surface such as the vagina.

Example 6

Mild Cooling Effect of Poloxamer Foam Formulation

Procedure: The compositions were prepared as follows:

1. A stock solution of Poloxamer was prepared as follows: 20 gr. of Poloxamer (407 or 188) was added to 80 gr. of cold water and mixed until dissolved.

2. 5 gr. from stock solution was taken and mixed with 94.3 gr. water at RT and then 0.7 gr. of xanthan gum was added and mixed until dissolved.

| Ingredient | % w/w | % w/w |
|---|---|---|
| Poloxamer 188 | 1.00 | |
| Poloxamer 407 | | 1.00 |
| Xanthan gum | 0.70 | 0.70 |
| water | 98.30 | 98.30 |
| Propellant (AP-70) propane, butane and isobutane mixture | 8.00 | 8.00 |
| Foam quality | G-E | G-E |
| Temperature * | ~18.5° C. | ~18.5° C. |
| Collapse time (sec.) | >300/G | >300/G |

Comments: It was unexpectedly noted that foams derived from compositions of two types of Poloxamers in combination with xantham gum caused a mild cooling sensation when applied to the hand with relatively low amounts of propellant. Such amounts of propellant do not normally result in a noticeable cooling effect in other foam formulations. The observation was then tested quantitatively. Without being limited by any theory this may be due to the unique properties of the Poloxamers to moderate the expansion rate of the foam so that some evaporation/release of propellant continues for a short period after expulsion from the canister.

Temperature test:

Room temperature was measured. Thermocouple was placed in a weighing plate and covered with foam. Temperature was monitored until no changed appeared (about 30 sec.)

Room temperature (RT) was ~20.5° C., which means both Poloxamer/polymer formulations have a similar "cooling effect".

Section F

Poloxamer Synergism

Example 7

Effect of Liquid vs. Solid Poloxamer and Mixture of Thereof

| Ingredient | 24 | 01 | 25 | 26 |
|---|---|---|---|---|
| Poloxamer 407 |  | 1.00 | 1.00 | 2.00 |
| Poloxamer 124 | 1.00 |  | 1.00 | 2.00 |
| Purified water | 99.00 | 99.00 | 98.00 | 94.00 |
| Total | 100.00 | 100.00 | 100.00 | 100.00 |
| Propellant A70 | 8.00 | 8.00 | 8.00 | 8.00 |

Results

|  | 24 | 01 | 25 | 26 |
|---|---|---|---|---|
| PFF |  |  |  |  |
| Viscosity | 0.00 | 7.00 | 0.00 | 0.00 |
| Viscosity (+8% pentane) | 0.00 | NM | 0.00 | 0.00 |
| pH | 5.54 | 6.78 | 6.18 | 6.26 |
| Foam |  |  |  |  |
| Foam Quality | poor | Fairly good | excellent | excellent |
| Odor | No odor | No odor | No odor | No odor |
| Shakability of PF after propellant addition | None | white | None | None |
| color | white | None | white | white |
| pH | 6.13 | 6.34 | 6.77 | 6.11 |
| Density | NM | NM | 0.044 | 0.035 |
| Collapse time | NM | NM | 50/P | 45/P |
| Drainage Time | NM | NM | 30 | 30 |
| Bubble size | 93 | 93 | 76 | 108 |
| Total dispense weight | 94.31 | NM | 96.15 | 97.26 |

Procedure: Polymers were mixed with water until fully dissolved. Liquid poloxamer was mixed with water at room temperature.

Comments: Foam quality was poor when liquid Poloxamer was used. A mixture of two Poloxamers, one liquid and the other solid, was able to produce foam of high quality. The formulation, however was not stable and was drained following 50 seconds. Surprisingly, the bubble size of the formulations with the liquid lower molecular weight Poloxamer was smaller compared to previous formulations using solid higher molecular weight Poloxamers. Total dispense weight was relatively high suggesting that PFF was dispensed using the propellant.

Section G

Poloxamer and Surfactants

Example 8

Foam Vehicle Composition Containing Poloxamer 407 and a Surfactant

| Ingredient | 09 | 10 | XXX |
|---|---|---|---|
| Poloxamer 407 % W/W | 1.00 | 1.00 | 1.00 |
| Poloxamer 407 (20%) | 5.00 | 5.00 | 5.00 |
| PEG100 stearate | 1.00 |  |  |
| Laureth 23 |  | 1.00 |  |
| Polysorbate 60 (surfactant) |  |  | 1.00 |
| Purified water | 94.00 | 94.00 | 94.00 |
| Total | 100.00 | 100.00 | 100.00 |
| Propellant A70 | 8.00 | 8.00 | 8.00 |

Results

|  | 09 | 10 | XXX |
|---|---|---|---|
| PFF |  |  |  |
| Viscosity | 0.00 | 0.00 | NM |
| Viscosity (+8% pentane) | 0.00 | 1.00 | NM |
| pH | 6.35 | 6.53 | NM |
| Foam |  |  |  |
| Foam Quality | Fairly good | Good | Excellent |
| Odor | NM | No odor | No odor |
| Shakability of PF after propellant addition | NM | None | shakable |
| color | white | white | white |
| pH | 6.34 | 6.24 | NM |
| Density | NM | 0.072 | NM |
| Collapse time | NM | >180/FG | >180/G |
| Drainage Time | NM | 150 | NM |
| Bubble size | 108 | 132 | NM |
| Total dispense weight | 87.59 | 97.44 | NM |

Procedure: Surfactant was dissolved in water with mixing at 50° C. The mixture was cooled to RT. Poloxamer 407 was added to the mixture with stirring until fully dissolved.

Comments: 1% Poloxamer 407 combined with 1% polysorbate 60 or Laureth 23, is sufficient to make high quality foam. The formulation has a synergistic foam forming effect since neither Poloxamer nor the surfactant at their current concentrations are sufficient to produce an acceptable foam, but their combination provides an excellent foam with high expansion (density of less that 0.1 g/mL), easy spreadability and quick absorption into the skin upon application. PEG 100 stearate which is a polyoxyethylene ester however failed to produce high quality foam in comparison to the alkyl ether (Laureth) and fatty acid esters (polysorbate).

Low concentrations of surfactant are an advantage, especially where the composition is to be applied to sensitive skin or mucosal surfaces in order to minimize skin or mucosal irritation. Repeated application of surfactants to the skin can result in depletion of fatty substances causing drying of the skin. So another advantage of very low surfactant levels is that even with repeated use drying of the skin is minimized or eliminated. Notably, in certain cases the concentration of 1% Poloxamer 407 is a limiting factor, due to both the FDA inactive ingredient list for topical administration which currently sets 1% as an upper limit; and secondly since the viscosity of the pressurized composition can interfere with shakability. By utilizing low polymer concentrations it can be easier to achieve greater shakability. Nevertheless, unexpectedly elsewhere formulations have been achieved with acceptable shakability despite formulations having high viscosity after the addition of propellant (See Examples 2A and 1F).

Section H

Silicones and Poloxamer

Example 9

Poloxamer Foamable Compositions with and without Different Silicones Added

|  | 092 | 092A | 092B | 092C |
|---|---|---|---|---|
| Ingredient |  |  |  |  |
| Poloxamer 407 Actual % W/W | 2.00 | 2.00 | 2.00 | 2.00 |
| Solution of Carbomer 947P 0.4% and Trolamine 0.2% | 90.00 | 87.50 | 87.50 | 87.50 |
| Poloxamer 407 20% sol. | 10.00 | 10.00 | 10.00 | 10.00 |
| Cyclomethicone |  |  | 2.50 |  |
| Dimethicone |  |  |  | 2.50 |
| Cyclomethicone and Dimethicone Copolyol (DC3225C) |  | 2.50 |  |  |
| Total | 100.00 | 100.00 | 100.00 | 100.00 |
| Propellant PFF | 8.00 | 8.00 | 8.00 | 8.00 |
| Centrifugation 3000 rpm/10 min | Stable | Stable | Stable | Stable |
| Centrifugation 10000 rpm/10 min | Stable | Pentane Separ. 5% | Pentane Separ. 5% | Pentane Separ. 10% |
| Viscosity, cP | 13,365.15 | NM | NM | NM |
| Foam |  |  |  |  |
| Foam quality | Good | Excellent | Excellent | Excellent |
| Foam density | 0.076 | 0.046 | 0.049 | 0.051 |
| Hardness, g | 23.37 | 21.97 | 22.65 | 22.61 |
| Collapse time, sec | >300 | NM | NM | NM |
| Foam drainage, sec | <60 | NM | NM | NM |
| Shakability of PF after propellant addition | Good | Good | Good | Good |
| pH direct | 5.00 | NM | NM | NM |
| pH diluted 1:5 | 4.58 | NM | NM | NM |
| Mean bubble size [micron] | 102 | NM | NM | NM |

Procedure: For procedure, see Example 10.

Comments: Surprisingly, despite the presence of silicone which is a defoaming agent the resultant compositions were of good to excellent quality. These compositions had improved stability. As is seen above and in Example 10 these compositions were all stable to the centrifugation test at 3000 rpm. At 10,000 rpm there appears to be some propellant separation when silicone was present. Interestingly and unexpectedly, the foam quality was also improved in the presence of the different silicones. Although silicones are known to be defoamers—without being bound by any theory—it may be assumed that they assist with propellant dissolution forming an emulsion formulation. It is noteworthy that whilst significant drainage occurs in the foam it nevertheless, has a collapse time of greater than 300 secs.

Example 10

Poloxamer Foamable Compositions Comprising Pemulen and Poloxamer with and without Different Silicone Additions

|  | 091 | 091A | 091B | 091C |
|---|---|---|---|---|
| Ingredient |  |  |  |  |
| Sol. Of Pemulen TR2 0.5% and Trolamine 0.5% | 90.00 | 87.50 | 87.50 | 87.50 |
| Poloxamer 407 % W/W | 2.00 | 2.00 | 2.00 | 2.00 |
| Poloxamer 407 20% sol | 10.00 | 10.00 | 10.00 | 10.00 |
| Cyclomethicone |  |  | 2.50 | — |
| Dimethicone |  |  |  | 2.50 |
| Cyclomethicone and Dimethicone Copolyol (DC3225C) |  | 2.50 |  |  |
| Total | 100.00 | 100.00 | 100.00 | 100.00 |
| Propellant AP-70 % | 8.00 | 8.00 | 8.00 | 8.00 |
| Results |  |  |  |  |
| Foam quality | Good | Excellent | Excellent | Excellent |
| Foam density, g/mL | 0.056 | 0.046 | 0.049 | 0.044 |
| Hardness, g | 24.61 | 22.40 | 24.12 | 24.29 |
| Collapse time, sec | >300 | NM | NM | NM |
| Foam drainage, sec | <60 | NM | NM | NM |
| Shakability of PF after propellant addition | Good | Good | Good | Good |
| pH direct | 6.38 | 6.65 | 6.51 | 6.67 |
| pH diluted 1:5 | 6.28 | 6.33 | 6.34 | 6.36 |
| Centrifugation 3000 rpm/10 min | Stable | Stable | Stable | Stable |
| Centrifugation 10000 rpm/10 min | Pentane Separ. 5% | Pentane Separ. 10% | Pentane Separ. 5% | Pentane Separ. 10% |
| Mean bubble size [micron] | 143 | NM | NM | NM |
| Viscosity, cP | 2,855.39 | NM | NM | NM |

Procedure:
1. Disperse Carbomer/Pemulen into highly agitated water.
2. Mix 20-30 min until complete dissolution of Carbomer/Pemulen.
3. Add Trolamine and mix 20-30 min until clear uniform gel is obtained.
4. Heat to 50-60° C. and add Dimethicone. (For the addition Cyclomethicone and Polyol silicones, heating is not required.

Comments: Good to excellent foam compositions were formed. These compositions were all stable to the centrifugation test at 3000 rpm. At 10,000 rpm there appears to be some propellant separation. Interestingly and unexpectedly, the foam quality was improved in the presence of the different silicones. Although silicones are known to be defoamers perhaps they assist with propellant dissolution and or Poloxamer interaction providing the formulation with an emulsion type format. It is noteworthy that drainage occurs in the foam even though it has a collapse time of greater than 300 secs. Interestingly, although, there is no major difference in bubble size of the foams and the bubbled gel (See Example 1), with the former perhaps having the larger average size, there is huge difference in quality of the foam released, which apparently is due to factors other than bubble size.

Section I

A Hydrophilic Solvent, a Hydrophobic Solvent and Poloxamer

Example 11A

Vehicle Composition, Containing Poloxamer 407, a Hydrophilic Solvent, a Non-Ionic Surfactant and a Hydrophobic Solvent

| Ingredient | Function | % w/w |
| --- | --- | --- |
| Poloxamer 407 (20% solution) | | 75.00 (15% Poloxamer) |
| Glycerin | Hydrophilic solvent, therapeutically effective solvent, emollient | 3.00 |
| Propylene glycol | hydrophilic solvent, therapeutically effective solvent, emollient | 3.00 |
| Polysorbate 80 | surfactant | 2.00 |
| Cyclomethicone | hydrophobic solvent; therapeutically effective solvent | 1.00 |
| Purified water | | To 100% |

Foam Properties

| Foam quality | Excellent |
| --- | --- |
| Color | white |
| Odor | no odor |
| Density (g/mL) | <0.1 |

Procedure:
1) A stock solution of 20% Poloxamer in H$_2$O was prepared.
2) The solution was cooled using ice bath while mixing to liquid (~15° C.).
3) 3 gr. glycerin, 3 g propylene glycol, 2 g Polysorbate 80 and 1 g cyclomethicone were added while mixing.
4) Water was added to complete weight of 100 g.

Comments: Interestingly, whilst polysorbate does not work well with carbopol (see Example 8A) it is successful with a hydrophobic/hydrophilic formulation comprising a silicone, a penetration enhancer (PG) and a humectant (glycerin)

Example 11B

Vehicle Composition, Containing Poloxamer 407, a Hydrophilic Solvent, a Non-Ionic Surfactant and Hydrophobic Solvents

| Ingredient | Function | % w/w |
| --- | --- | --- |
| Heavy mineral oil | hydrophobic solvent, emollient | 6.00 |
| Poloxamer 407 (20% solution) | | 75.00 (15% poloxamer) |
| Glycerin | Hydrophilic solvent, therapeutically effective solvent, emollient | 3.00 |
| Propylene glycol | hydrophilic solvent, therapeutically effective solvent, emollient | 3.00 |
| Sorbitan oleate | surfactant | 2.00 |
| Cyclomethicone | hydrophobic solvent; therapeutically effective solvent | 1.00 |
| Purified water | | To 100% |

Foam Properties

| Foam quality | Excellent |
| --- | --- |
| Color | white |
| Odor | no odor |
| Density (g/mL) | <0.1 |

Procedure:
1) A stock solution of 20% Poloxamer in H$_2$O was prepared.
2) The solution was cooled using ice bath while mixing to liquid (~15° C.).
3) 3 gr. glycerin, 3 g propylene glycol, 2 g Sorbitan oleate, Heavy mineral oil and 1 g cyclomethicone were added while mixing.
4) Water was added to complete weight of 100 g.

Comments: The addition of mineral oil did not affect foam quality.

B THERAPEUTIC EXAMPLES

Section 1

Diclofenac and Poloxamer

Example 12A

Aqueous Composition, Containing Poloxamer 407 and Diclofenac as Active Agent

| Ingredient | % w/w |
| --- | --- |
| Poloxamer 407 (20% solution) | 75.00 |
| Glycerin | 3.00 |
| Propylene glycol | 3.00 |
| Polysorbate 80 | 2.00 |
| Sodium diclofenac | 3.00 |
| Cyclomethicone | 1.00 |
| Purified water | 13.00 |
| Total: | 100.00 |

Procedure (to make 100 gr):
1. A stock solution of 20% Poloxamer in H$_2$O was prepared.
2. 75 gr. of the stock solution were heated to 75° C. 3 gr. of sodium diclofenac was then added while mixing until complete dissolution.
3. The solution was cooled using ice bath while mixing to liquid (~15° C.).
4. 3 gr. glycerin, 3 gr. Propylene glycol, 6 gr. Heavy mineral oil, 2 gr. Polysorbate 80 and 1 gr. Cyclomethicone were added while mixing.
5. Water was added to complete weight of 100 gr.

Aqueous Composition Properties

| | |
|---|---|
| Centrifugation (10,000 RPM) | stable |
| pH (direct) | 8.31 |
| pH (1:5) | 8.00 |

Comments: The vehicle of Example 11A with active ingredient is stable on centrifugation indicating good resistance to aging.

Example 12B

Emulsion Composition, Containing Poloxamer 407 and Diclofenac as Active Agent

| Ingredient | % w/w |
|---|---|
| Heavy mineral oil | 6.00 |
| Glycerin | 3.00 |
| Propylene glycol | 3.00 |
| Sorbitan oleate | 2.00 |
| Poloxamer 407 (20% solution) | 75.00 |
| Sodium diclofenac | 3.00 |
| Purified water | 7.00 |
| Cyclomethicone | 1.00 |
| Total: | 100.00 |

Procedure:
1. A stock solution of 20% Poloxamer in $H_2O$ was prepared.
2. 75 gr. of the stock solution were heated to 75° C. 3 gr. of sodium diclofenac were then added while mixing until complete dissolution.
3. The solution was cooled using ice bath while mixing to liquid (~15 C).
4. 3 gr. glycerin, 3 gr Propylene glycol, 6 gr. Heavy mineral oil, 2 gr. sorbitan oleate and 1 gr. Cyclomethicone were added while mixing.
5. Water was added to complete weight of 100 gr.

Emulsion Properties

| | |
|---|---|
| Centrifugation (10,000 RPM) | Stable |
| pH (direct) | 8.00 |
| pH (1:5) | 8.01 |

Comments: The vehicle of Example 11B with active ingredient is stable on centrifugation indicating good resistance to aging.

Example 12C

Poloxamer Composition with Diclofenac Sodium: Solubility

Poloxamer 407 functions as co-solubilizer ingredient of sodium diclofenac. When included in the formulation at 15% concentration, crystals were not observed under the microscope.

| Ingredient | 001 | 002 |
|---|---|---|
| Sodium diclofenac | 3.00 | 3.00 |
| Poloxamer 407 | 15.00 | 15.00 |
| Heavy mineral oil | | 6.00 |
| Glycerine | 3.00 | 3.00 |
| Propylene glycol | 3.00 | 3.00 |
| Polysorbate 80 | 2.00 | |
| Sorbitan laurate | | 2.00 |
| Cyclomethicone | 1.00 | |
| Purified water | 73.00 | 68.00 |
| Total | 100.00 | 100.00 |
| Propellant (AP-70) | 8 | 8 |

Foam properties (T-0)

| | | |
|---|---|---|
| Assay (by HPLC) | 2.95 | 3.03 |
| Foam quality | Excellent | Good |
| Color | White | White |
| Odor | No odor | No odor |
| Collapse time (sec) | >300/G | >300/G |
| Density | 0.047 | 0.052 |
| Bubble size | 106.00 | 75.00 |
| Bubble size (above 500)μm | 0.0 | 0.0 |
| Microscope for NaDiclofenac crystals | Not observed | Not observed |

Stability: Foam Properties Following Four Freeze & Thaw Cycles

| | | |
|---|---|---|
| Foam quality | Excellent | Good |
| Color | White | White |
| Odor | Very faint | Very faint |
| Microscope for NaDiclofenac crystals | Not observed | Not observed |

Stability: Foam Properties Following 1 Month at 5° C.

| | | |
|---|---|---|
| Assay (by HPLC) | 3.04 | 3.07 |
| Foam quality | Excellent | Good |
| Color | White | White |
| Odor | No odor | No odor |
| Collapse time | >300/G | >300/G |
| Density | 0.047 | 0.052 |
| Microscope for NaDiclofenac crystals | Not observed | Not observed |
| pH | 3.04 | 3.07 |

Stability: Foam Properties Following 1 Month at 40° C.

| | | |
|---|---|---|
| Foam quality | Excellent | Good |
| Color | White | White |
| Odor | No odor | No odor |
| Microscope for NaDiclofenac crystals | Not observed | Not observed |

Stability: Foam Properties Following 2 Months at 5° C.

| | | |
|---|---|---|
| Foam quality | Excellent | Good |
| Color | White | White |
| Odor | No odor | No odor |
| Microscope for NaDiclofenac crystals | Not observed | Not observed |

Stability: Foam Properties Following 1 Month at 40° C.

| Foam quality | Excellent | Good |
|---|---|---|
| Color | White | White |
| Odor | No odor | Very faint odor |
| Collapse time | >300/G | >300/G |
| Density | 0.065 | 0.068 |
| Microscope for NaDiclofenac crystals | Not observed | Not observed |
| pH | 3.09 | 3.29 |

Stability: Foam Properties Following 3 Months at 5° C.

| Foam quality | Excellent | Good |
|---|---|---|
| Color | White | White |
| Odor | No odor | No odor |
| Microscope for NaDiclofenac crystals | Not observed | Not observed |

Stability: Foam Properties Following 3 Months at 40° C.

| Foam quality | Excellent | Good |
|---|---|---|
| Color | White | White |
| Odor | No odor | Very faint odor |
| Collapse time | >300/G | >300/G |
| Density | 0.079 | 0.068 |
| Microscope for NaDiclofenac crystals | Not observed | Not observed |
| pH | 2.96 | 2.97 |

Procedure:
1. POLA 001 was prepared as described in Example 12A+8% propellant for producing foam
2. POLA 002 was prepared as described in Example 12B+8% propellant for producing foam Comments: Both pharmaceutical formulations with and without mineral oil were observed to be chemically and physically stable over a period of three months in accelerated stability studies even at an elevated temperature of 40° C. Note: In order to assess the concentration of Poloxamer 407 which is required to afford full solubility of the active agent, 3% sodium diclofenac was added to 5, 7 and 10 percent of Poloxamer in water. All 3 concentrations were heated to 75° C. to dissolution and cooled. In all cases, after 24 h, crystals were visually observed Example 12D In-Vitro Penetration Study of 3% (w/w) Diclofenac Foam Product, in Comparison with Solaraze The aim of this study was to compare the in vitro penetration of Diclofenac Foam formulated at 3% (w/w) to one commercial reference product (Solaraze® Gel, 3% w/w) across ear pig skin.
Formulations Tested:
1. Solaraze Gel, 3% (w/w)
2. Diclofenac Foam, POLA001 3% (w/w)
3. Diclofenac Foam, POLA0023% (w/w)
Experimental Conditions:
Absorption studies were conducted using excised pig ear skin mounted onto a flow-through diffusion cell over a 24-hour period. Four skin samples for each foam formulation and three skin samples of Solaraze gel were used. A target amount of 1 g of each formulation (30 mg of Diclofenac) was applied to a skin surface of 1.77 $cm^2$. Concentrations of Diclofenac in receptor fluid fractions over time and remaining in the skin at the end of the study were assayed using an HPLC method with UV detection. The limit of quantification was 20 $ng/mL^{-1}$.

Samples analyzed for Diclofenac content:

1. Stratum Corneum—obtained by 19 tape-stripping.
2. Viable skin ("Skin Extraction"; skin section remaining after test stripping).
3. Receptor fluid (Transdermal Delivery).

As shown in FIG. 1, the experimental results showed that the two formulations of Diclofenac Foam as well as the Solaraze gel formulation continuously diffused into the receptor fluid (RC) over the time-course of the experiment. The quantities of active ingredient recovered in the skin and receptor fluid at the end of the study (24 h) were:

Diclofenac foam, 3% (w/w)—Prototype 001

Penetrated amount: 338.4 $\mu g/cm^2$ for Stratum Corneum and 7.4 $\mu g/cm^2$ for Skin Extraction (Total Skin content=345.8 $\mu g/cm^2$)

Transdermal Delivery: 81.44 $\mu g/cm^2$

Diclofenac foam, 3% (w/w)—Prototype 002

Penetrated amount: 360.2 $\mu g/cm^2$ for Stratum Corneum and 4.0 $\mu g/cm^2$ for Skin Extraction (Total Skin content=364.2 $\mu g/cm^2$)

Transdermal Delivery: 55.12 $\mu g/cm^2$

Solaraze Gel, 3% (w/w)

Intradermal penetration: 128.6 $\mu g/cm^2$ for Stratum Corneum and 34.7 $\mu g/cm^2$ for Skin Extraction (Total Skin content=163.3 $\mu g/cm^2$)

Transdermal Delivery: 50.49 $\mu g/cm^2$.

In FIG. 1, "RC" refers to Diclofenac found in the Receiving Compartment (receptor fluid). "Total skin" refers to Diclofenac found in the viable skin extraction+the tape stripping samples. "Skin Extraction" refers to Diclofenac found only in the skin extraction.

Conclusions:

1. Intradermal Penetration:
   a. The concentration of Diclofenac in the skin was about two times greater for both foam formulations, compared with Solaraze. This difference was statistically significant Prototype 001 (T-Test, p=0.048); and marginally significant for Prototype 002 (p=0.063).
   b. Most of the Diclofenac was found in the Stratum Corneum, which is the reservoir of active material, to be further released into the viable skin.
   c. There a trend toward a higher concentration of Diclofenac in the Skin Extract for Solaraze, however, according to F-test, the populations were not statistically different (T-Test, p=0.41 and p=0.37).
2. Transdermal Delivery:
   a. The transdermal delivery of Diclofenac from all three preparations was essentially similar (T-Test, p=0.36 and p=0.86).
   b. The ratio between the intradermal penetration and transdermal delivery was higher for Prototype 001 and Prototype 002 foam formulations compared with Solaraze (4.2, 6.6 and 3.2 respectively), indicating intradermal preference for the foam formulations.

Example 12E

Aqueous Composition, Containing Poloxamer 188 and Diclofenac as Active Agent

| Ingredient | % w/w |
|---|---|
| Sodium diclofenac | 3.00 |
| Poloxamer 188 (20% solution) | 75.00 |
| Glycerin | 3.00 |
| Propylene glycol | 3.00 |
| Polysorbate 80 | 2.00 |
| Cyclomethicone | 1.00 |
| Purified water | 13.00 |
| Total: | 100.00 |

Foam Properties:

| Results T-0 | |
|---|---|
| Foam quality | E |
| Color | white |
| Odor | no odor |
| Shakability of PF after propellant addition | 0 |
| Collapse time | 100/F |
| Bubble size | 114.00 |
| Bubble size (above 500) μm | 3.3 |
| Microscope (crystals only) | not observed |
| Results FTC | |
| Foam quality | E |
| Color | white |
| Odor | no odor |
| Shakability | 1 |
| Microscope (crystals only) | not observed |

Procedure:
1. A stock solution of 20% Poloxamer 188 in H$_2$O was prepared.
2. 75 gr. of the stock solution were heated to 75° C. 3 gr. of sodium diclofenac were then added while mixing until complete dissolution.
3. The solution was cooled using ice bath while mixing to liquid (~15 C).
4. 3 gr. glycerin, 3 gr Propylene glycol, 6 gr. Heavy mineral oil, 2 gr. Polysorbate 80 and 1 gr. Cyclomethicone were added while mixing.
5. Rests of water were added to complete weight of 100 gr.

Example 12F

Emulsion Composition, Containing Poloxamer 188 and Diclofenac as Active Agent

| Ingredient | % w/w |
|---|---|
| Heavy mineral oil | 6.00 |
| Glycerin | 3.00 |
| Propylene glycol | 3.00 |
| Sorbitan oleate | 2.00 |
| Poloxamer 188 (20% solution) | 75.00 |
| Sodium diclofenac | 3.00 |
| Purified water | 7.00 |
| Cyclomethicone | 1.00 |
| Total: | 100.00 |

Foam Properties:

| Results T-0 | |
|---|---|
| Foam quality | E |
| Color | white |
| Odor | no odor |
| Shakability of PF after propellant addition | 1 |
| Collapse time | 270/FG |
| Bubble size | 101.00 |
| Bubble size (above 500) μm | 0.0 |
| Microscope (crystals only) | not observed |
| Results FTC | |
| Foam quality | G |
| Color | white |
| Odor | no odor |
| Shakability | 1 |
| Microscope (crystals only) | not observed |

Procedure:
6. A stock solution of 20% Poloxamer in H$_2$O was prepared.
7. 75 gr. of the stock solution were heated to 75° C. 3 gr. of sodium diclofenac were then added while mixing until complete dissolution.
8. The solution was cooled using ice bath while mixing to liquid (~15 C).
9. 3 gr. glycerin, 3 gr Propylene glycol, 6 gr. Heavy mineral oil, 2 gr. sorbitan oleate and 1 gr. Cyclomethicone were added while mixing.
10. Rests of water were added to complete weight of 100 gr.

Comments: Whilst lower average molecular weight Poloxamer 188 produces a therapeutic foam formulation of excellent quality that can withstand FTC testing for hydrophilic hydrophobic formulations with and without mineral oil, higher average molecular weight Poloxamer 407 produces therapeutic foam formulations that have improved collapse times.

Section 2

Salicylic Acid and Poloxamer

Example 13

Poloxamer Composition with Salicylic Acid: Solubility

Description:
In both vials, 1 & 2, there are 12.5 gr. of 20% Poloxamer 188/purified water stock solution (2.5 gr. Poloxamer 188+10 gr. purified water).

In vial #1, 0.25 gr. of salicylic acid was dissolved (1:10 ratio API/Poloxamer 188, 1:40 ratio API/purified water).

In vial #2, 0.50 gr. of salicylic acid was dissolved (1:5 ratio API/Poloxamer 188, 1:20 ratio API/purified water).

Figure 2:
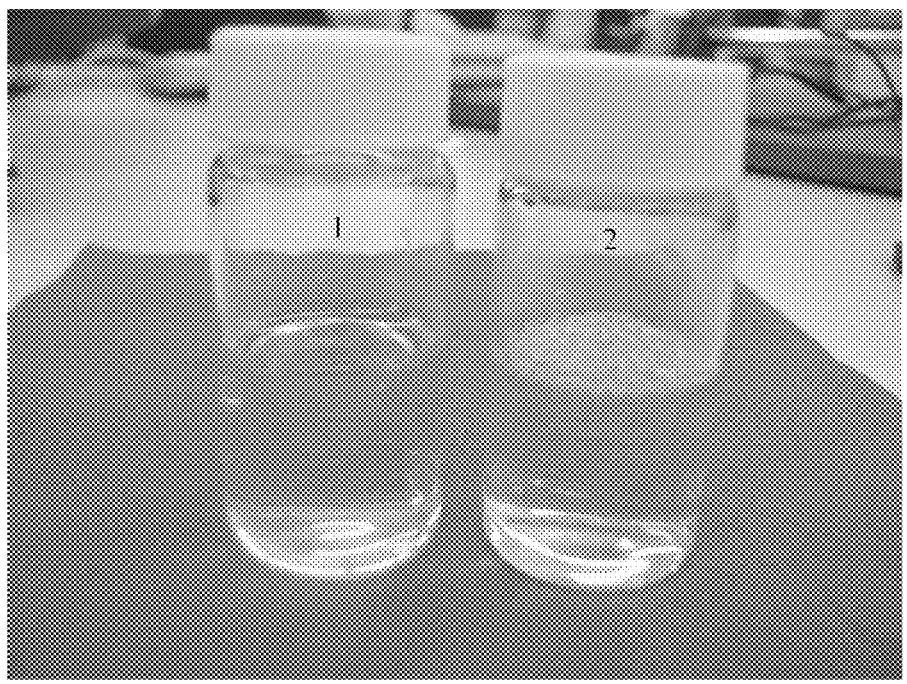
FIG. 2 is a photograph illustrating the gel inducing effect of salicylic acid on a poloxamer containing formulation according to one or more embodiments by showing two vials in a vertical perspective with different concentrations of salycilic acid.
Figure 3:
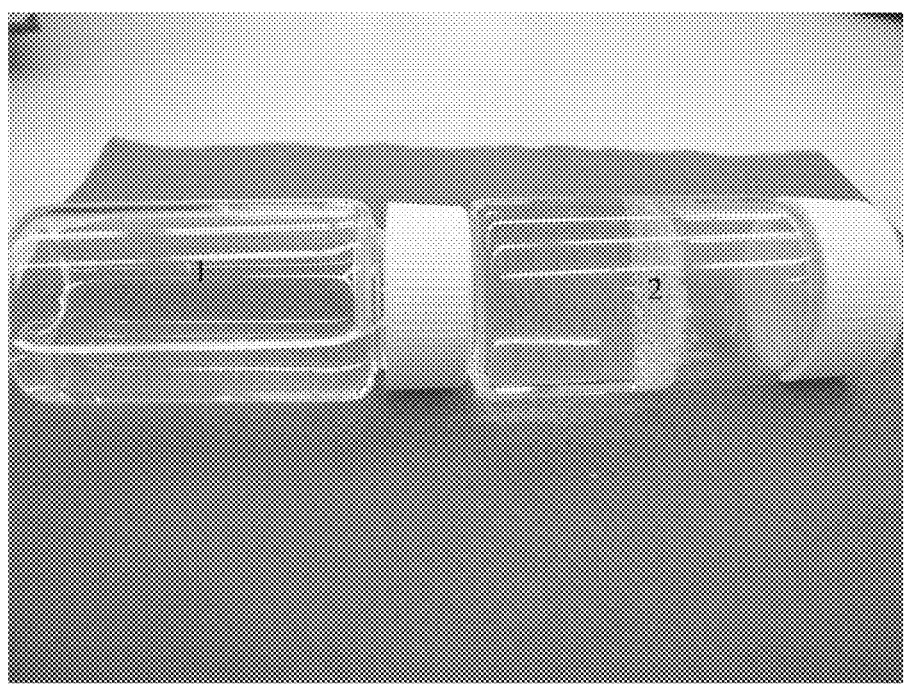
FIG. 3 is a photograph illustrating the gel inducing effect of salicylic acid on a poloxamer containing formulation according to in one or more embodiments by showing two vials in a horizontal perspective with different concentrations of salycilic acid.

Comments: As shown clearly in FIG. 2 and FIG. 3, the vial on the right side with a doubled salicylic acid concentration compared to the stock solution in the vial on the left hand side, produced viscous gel with no fluidity, while salicylic acid is completely dissolved in both cases.

According to literature (USP 29), Salicylic acid's solubility in water is 1 gr. in 460 gr. (~0.2% at 20° C.). Unexpectedly, Poloxamer 188 multiplied solubility of Salicylic acid in water by about 25.

Section 3

Other Active Agents and Poloxamer

Example 14

Poloxamer Composition with Various Active Agents

|  | % w/w Salicylic acid foam | % w/w Clindamycin foam | % w/w Acyclovir foam | % w/w Minoxidil foam | % w/w Benzoyl Peroxide foam |
|---|---|---|---|---|---|
| Salicylic acid | 3.85 | | | | |
| Clindamicin Phosphate | | 0.79 | | | |
| Acyclovir | | | 3.85 | | |
| Minoxidil | | | | 3.85 | |
| Benzoyl Peroxide | | | | | 4.58 |
| Poloxamer 188 | 19.23 | 19.84 | 19.23 | 19.23 | 19.08 |
| Purified water | 76.92 | 79.37 | 76.92 | 76.92 | 76.34 |
| Total | 100.00 | 100.00 | 100.00 | 100.00 | 100.00 |
| Microscope observation | No crystals | No crystals | crystals | crystals | crystals |

Comments: The poloxamer carriers are suitable for use both with active agents that can be solubilized and also with suspensions of active agents.

Section 4

Prophetic Examples of Poloxamer with Microsponges or Therapeutic Cells

Example 15A

Prophetic Foamable Compositions Comprising Microsponges

|  | 1 % w/w | 2 % w/w | 3 % w/w | 4 % w/w |
|---|---|---|---|---|
| Sol. Pemulen 0.5% (&) Trolamine 0.5% (&) Poloxamer 407 2% | 95.00 | 95.00 | — | — |
| Sol. Carbomer 974P 0.4% (&) Trolamine 0.2% (&) Poloxamer 407 2% | — | — | 92.50 | 92.50 |
| Cyclomethicone Dimethicone | — | — | 2.50 | 2.50 |
| Cyclomethicone and Dimethicone Copolyol (DC3225C) | — | — | — | — |
| Microsponge polymer | 5.00 | 5.00 | 5.00 | 5.00 |
| Made up with water to 100%: | 100.00 | 100.00 | 100.00 | 100.00 |
| Propellant AP-70% | 8-00 | 8-00 | 8-00 | 8-00 |

Example 15B

Prophetic Foamable Compositions Comprising Microsponges

|  | 1 % w/w | 2 % w/w | 3 % w/w | 4 % w/w |
|---|---|---|---|---|
| Sol. Pemulen 0.5% (&) Trolamine 0.5% (&) Poloxamer 407 2% | 92.50 | 92.50 | — | — |
| Sol. Carbomer 974P 0.4% (&) Trolamine 0.2% (&) Poloxamer 407 2% | — | — | 92.50 | 92.50 |
| Cyclomethicone Dimethicone | 2.50 | 2.50 | — | — |
| Cyclomethicone and Dimethicone Copolyol (DC3225C) | — | — | 2.50 | 2.50 |
| Microsponge polymer | 5.00 | 5.00 | 5.00 | 5.00 |
| Made up with water to 100%: | 100.00 | 100.00 | 100.00 | 100.00 |
| Propellant AP-70 | 8-00 | 8-00 | 8-00 | 8-00 |

Comments: The prophetic foam formulations may have properties not too dissimilar to the carrier formulations to which the microsponges have been added.

Prophetic Example 16

Poloxamer/Polymer Vehicle Gel Compositions with Therapeutic Cells

The following table provides possible compositions of a therapeutic cell and two exemplary Poloxamer/polymer systems. The compositions are suitable for application onto any body surface, including for example the skin, the vagina, any body cavity and any mucosal surface. They can be suitable as carriers of various therapeutic cells including but not limited to fibroblasts, langerhans cells, keratinocytes, leukocytes, phagocytes (such as macrophages, neutrophils, and dendritic cells), mast cells, eosinophils, basophils, and natural killer cells. Without limiting the scope of this invention, by selecting certain therapeutic cells, the compositions are useful for the treatment of a disease or disorder, which involve microbial, bacteria, fungal or viral infection, autoimmune conditions, tumors, metastases, wound, burn, ulcer, post operative injury and any further disease or disorder, which is responsive to treatment with such therapeutic cells.

| | | |
|---|---|---|
| Poloxamer 407 | 20% | 5% |
| Xanthan gum | | 0.5% |
| Macrophage*/suitable aqueous medium | To 100% | To 100% |
| Prophetic Behavior on hand (PFF at RT) | Gel | Gel |

*or any other therapeutic cell. In another embodiment fractions or fragments of therapeutic cells may be used.

The compositions are packaged in a container, suitable for delivering a flowable composition to a target site. Alternatively, the compositions can be packaged in an aerosol container, equipped with a valve and an actuator, capable of releasing a foam and pressurized with a liquefied or compressed propellant at a concentration of about 1% to about 25% by weight of the total composition. In other embodiments a bag in can or bag on valve system is used. In further embodiments a dual chamber system is used where the cells are in one chamber (bag in canister where the propellant is separate from the cells) and the Poloxamer formulation is in a separate canister in the other chamber. Upon actuation the two compositions are expelled and are mixed either in a mixing chamber or in the passage connected to the canisters or outside the dual canister system.

Preparation of Formulations with therapeutic cells and Poloxamer.
1.) Prepare a Poloxamer formulation as described herein such that after step 4 the Poloxamer will be at the required concentration
2) Isolate and or culture therapeutic cells according to known techniques, for example as detailed in Cell Culture Technology for Pharmaceutical and Cell-based Therapies By Sadettin S. Ozturk, Wei-Shou Hu Published 2005 and also in Practical Cell Culture Techniques By Alan A. Boulton, Glen B. Baker, Wolfgang Walz, Published 1992, Humana Press, both of which are incorporated by reference.
3) Obtain and Suspend a concentrate of therapeutic cells in an appropriate medium compatible with the cells and the Poloxamer formulation
4.) When the Poloxamer formulation is at room temperature, and is still liquid, therapeutic cells are added and the formulation is gently mixed for about 5 to about 10 minutes until homogenous.

What is claimed is:
1. A pharmaceutical or cosmetic composition comprising:
a. water;
b. at least two poloxamers at a concentration of about 0.1% to about 5% by weight of the composition:
c. one or more active agents,
wherein the composition is pressurized with a liquefied or compressed propellant;
wherein the weight ratio of the composition to the propellant is about 100:5 to about 100:25;
wherein the at least two poloxamers are a synergistic combination of at least one liquid poloxamer and at least one solid poloxamer; and
wherein the one or more active agents are soluble in the composition.

2. The composition of claim 1, wherein the poloxamers are selected from the group consisting of poloxamer 124, poloxamer 188, poloxamer 237, poloxamer 338, poloxamer 407, and mixtures of two or more thereof.

3. The composition of claim 1, wherein the composition is capable of affording a fixing effect on application to a body surface at 30° C. or more.

4. The composition of claim 1, wherein the at least two poloxamers are at a total amount of about 0.2% to about 2% by weight of the composition.

5. The composition of claim 1, wherein at least one of the two poloxamers comprises a molecular weight in a range (i) between about 2,000 and about 2,400; or (ii) between about 6,800 and about 8,900; or (iii) between about 7,600 and about 9,500; or (iv) between about 9,800 and about 14,600; or (v) between about 12,000 and about 18,000.

6. The composition of claim 1, further comprising a non-ionic surface active agent, wherein the ratio of the at least two poloxamers to non-ionic surface active agent is selected from about 1:2; about 1:1; about 2:1; about 4:1; about 8:1; about 10:1; about 15:1; about 20:1; about 30:1; about 40:1 to about 50:1; from about 1:2 to about 50:1; from about 1:1 to about 1:50; from about 2:1 to about 50:1; from about 4:1 to about 50:1; from about 8:1 to about 50:1; from about 10:1 to about 50:1; from about 15:1 to about 50:1; from about 20:1 to about 50:1; from about 30:1 to about 50:1; from about 40:1 to about 50:1; from about 1:2 to about 1:1; from about 1:2 to about 2:1; from about 10:1 to about 50:1; and from about 2:1 to about 8:10.

7. The composition of claim 1, further comprising a polymer or a polysaccharide, wherein the ratio of the at least two poloxamers to polymer or polysaccharide is selected from about 1:1; about 2:1; about 4:1; about 8:1; about 10:1; about 15:1; about 20:1; about 30:1; about 40:1 to about 50:1 from 1:1 to about 50:1; from about 1:2 to about 50:1; from about 1:1 to about 1:50; from about 2:1 to about 50:1; from about 4:1 to about 50:1; from about 8:1 to about 50:1; from about 10:1 to about 50:1; from about 15:1 to about 50:1; from about 20:1 to about 50:1; from about 30:1 to about 50:1; from about 40:1 to about 50:1; from about 1:2 to about 1:1; from about 10:1 to about 50:1; from about 2:1 to about 8:10.

8. The composition of claim 1, wherein the viscosity of the composition at about body temperature is greater than the viscosity of the composition at room temperature.

9. The composition of claim 1, wherein the percentage by weight of the composition of polyoxyethylene component of the at least two poloxamers is between about 70% and about 85% of at least one of the two poloxamers.

10. The composition of claim 1, wherein a foam produced from the composition has a mild cooling effect or sensation.

11. The composition of claim 1, wherein the intradermal penetration of the active agent is in excess of about 300 micrograms/cm$^2$/24 hr; or wherein the at least two poloxamers improve the absorption of the active agent into the stratum corneum and thereafter into the dermis without an increase in transdermal penetration.

12. The composition of claim 1, wherein the at least two poloxamers are included in the composition in an amount sufficient to dissolve an active agent in an aqueous phase, wherein such an active agent is not fully soluble in said aqueous phase, or wherein the active agent is not otherwise fully soluble in water, in hydrophobic solvent, or in an oil phase of an emulsion and the at least two poloxamers are present in the composition in an amount sufficient to solubilize the active agent in the composition; and wherein the active agent comprises at least one of diclofenac, salicylic acid, clindamycin or mixtures of two or more thereof.

13. The composition of claim 1, wherein the active agent in an effective amount is capable of causing the composition to form a gel, which in the presence of a sub-effective amount would be liquid.

14. The composition of claim 13, wherein the gelling effect is a result of a reduction in pH.

15. The composition of claim 1, further comprising at least one ingredient, comprising:
   a. about 1% to about 50% by weight of the composition of a hydrophobic solvent;
   b. about 1% to about 50% by weight of the composition of a non-volatile hydrophilic solvent;
   c. a foam adjuvant; or
   d. about 1% to about 10% by weight of the composition of a volatile hydrophilic solvent;
   or mixtures of two or more thereof;
   wherein the foam adjuvant comprises a fatty alcohol having 15 or more carbons in their carbon chain; or a fatty acid having 16 or more carbons in its carbon chain;
   or a fatty alcohol, derived from beeswax and including a mixture of alcohols, a majority of which have at least 20 carbon atoms in their carbon chains; or a fatty alcohol having at least one double bond; or a fatty acid having at least one double bond; or a branched fatty alcohol; or a branched fatty acid or a fatty acid substituted with a hydroxyl group; or a mixture of two or more thereof.

16. The composition of claim 15, wherein the composition is an oil in water emulsion.

17. The composition according to claim 1, further comprising a polymeric agent or a polysaccharide, wherein the at least two poloxamers and the polymeric agent or polysaccharide when present together act synergistically so that the amount of the at least two poloxamers required can be reduced.

18. The composition according to claim 1, further comprising a polymeric agent or a polysaccharide, wherein the polymeric agent or polysaccharide is water soluble or water dispersible.

19. The composition according to claim 1, wherein the composition comprises about 95% or more than 95% by weight of the composition of water.

20. The composition according to claim 18, wherein said at least one water-soluble or water dispersible polymeric agent or polysaccharide comprises one or more of an acrylic acid polymer, an acrylate/C10-30 alkyl acrylate crosspolymer, a carbomer, a methocel, a sodium carboxymethylcellulose, a polyvinylpyrrolidone, a xanthan gum or a mixture of two or more thereof.

21. A pharmaceutical or cosmetic foamable composition for application to a delivery site in a subject, the composition comprising:
   A. a carrier comprising:
      a. about 5% to about 20% by weight of the carrier of at least two poloxamers;
      b. water;
      c. about 0.2% to about 15% by weight of the carrier of at least one hydrophobic solvent;
      d. about 0.5% to about 5% by weight of the carrier of at least one surfactant;
      e. about 0.5% to about 15% by weight of the carrier of at least one hydrophilic solvent;
      f. one or more active agents, which optionally may be encapsulated; and
   B. a propellant,
      wherein the composition is stored in an aerosol container and upon release expands to form a breakable short term stable foam;
      wherein the weight ratio of the carrier to the propellant is about 100:5 to about 100:25;
      wherein the at least two poloxamers are a synergistic combination of at least one liquid poloxamer and at least one solid poloxamer; and
      wherein the one or more active agents are soluble in the composition.

22. The composition of claim 21, wherein the at least one hydrophobic solvent comprises at least one silicone compound.

23. The composition according to claim 22, wherein said at least one silicone compound comprises one or more of a cyclomethicone, a dimethicone, or a cyclomethicone and a dimethicone copolyol.

24. The composition of claim 22, further comprising an oil.

25. The composition of claim 21, wherein the hydrophilic solvent comprises a glycol, glycerin, or mixtures thereof.

26. The composition of claim 25, wherein the hydrophilic solvent comprises a glycol and glycerin, and the intradermal penetration of the active agent is in excess of about 300 micrograms/cm$^2$/24 hr; or wherein the at least two poloxamers improve the absorption of the active agent into the stratum corneum and thereafter into the dermis without an increase in transdermal penetration.

27. A method of treating or alleviating a disorder of a mammalian subject in need thereof, comprising administering a gel or foam produced from the composition of claim 12 to an area of skin or mucosa of said mammalian subject having said disorder, wherein the disorder is selected from the group consisting of one or more of pain, dermatological inflammation, acne, dermatitis, bacterial skin infections, cellulitis, cutaneous abscesses, folliculitis, furuncles, impetigo, warts, eczema, keratosis, and skin ulcers.

28. The composition of claim 1, wherein the composition is administered as a gel or a foam.

29. A pharmaceutical or cosmetic composition comprising either:
   A.
      a. water;
      b. at least two poloxamers at a concentration of about 0.1% to about 15% by weight of the composition:
   B.
      a. about 5% to about 20% by weight of the composition of at least two poloxamers;
      b. about 79% to about 93.8% of the composition of water;
      c. about 0.2% to about 15% by weight of the composition of at least one hydrophobic solvent;
      d. about 0.5% to about 5% by weight of the composition of at least one surfactant; and
      e. about 0.5% to about 15% by weight of the composition of at least one hydrophilic solvent; or
   C.
      a. about 1% to about 20% by weight of the composition of at least two poloxamers;
      b. 0% to about 5% by weight of the composition of at least one polymeric agent;
      c. about 79% to about 99% of the composition of water;

d. 0% to about 5% by weight of the composition of at least one silicone; and e. 0% to about 5% by weight of the composition of at least one surfactant;

wherein A, B or C are pressurized with a liquefied or compressed propellant;

wherein the weight ratio of the composition to the propellant is about 100:5 to about 100:25; and wherein the at least two poloxamers are a synergistic combination of at least one liquid poloxamer and at least one solid poloxamer.

30. The composition of claim 1, wherein the one or more active agents are encapsulated in microspheres.

31. The composition of claim 13, wherein the gelling effect is a result of an increase of ionic strength.

* * * * *

UNITED STATES PATENT AND TRADEMARK OFFICE
CERTIFICATE OF CORRECTION

PATENT NO.        : 8,709,385 B2
APPLICATION NO.   : 12/836444
DATED             : April 29, 2014
INVENTOR(S)       : Tamarkin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 162 days.

Signed and Sealed this
Eleventh Day of August, 2015

Michelle K. Lee
*Director of the United States Patent and Trademark Office*